United States Patent
Wang et al.

(10) Patent No.: US 10,335,029 B2
(45) Date of Patent: Jul. 2, 2019

(54) OPTHALMOSCOPE DEVICE

(71) Applicant: Welch Allyn, Inc., Skaneateles Falls, NY (US)

(72) Inventors: Ynjiun Paul Wang, Cupertino, CA (US); Ervin Goldfain, Syracuse, NY (US); Eric G. Petersen, Aloha, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 15/971,693

(22) Filed: May 4, 2018

(65) Prior Publication Data

US 2018/0249907 A1 Sep. 6, 2018

Related U.S. Application Data

(63) Continuation of application No. 15/662,363, filed on Jul. 28, 2017, now Pat. No. 10,159,409, which is a
(Continued)

(51) Int. Cl.
*A61B 3/14* (2006.01)
*A61B 3/10* (2006.01)
(Continued)

(52) U.S. Cl.
CPC .............. *A61B 3/12* (2013.01); *A61B 3/0008* (2013.01); *A61B 3/0025* (2013.01);
(Continued)

(58) Field of Classification Search
CPC ........... A61B 3/152; A61B 3/14; A61B 3/102; A61B 3/12; A61B 3/0025
(Continued)

(56) References Cited

U.S. PATENT DOCUMENTS 5,048,946 A 9/1991 Sklar et al.
5,557,350 A 9/1996 Yano
(Continued)

FOREIGN PATENT DOCUMENTS

CN 102324014 A 1/2012
CN 102626304 A 8/2012
(Continued)

OTHER PUBLICATIONS

Brown et al, "Comparison of image-assisted versus traditional fundus examination," Eye and Brain, Dovepress, Feb. 2013, vol. 5, pp. 1-8.
(Continued)

*Primary Examiner* — Mohammed A Hasan
(74) *Attorney, Agent, or Firm* — Merchant & Gould P.C.

(57) ABSTRACT

An example eye fundus imaging apparatus can include: a display device; an image capture device configured to capture at least one image of a fundus of an eye; and a control module programmed to: display a target, the target indicating a desired position for the image capture device to capture the at least one image of the fundus of the eye; monitor a relative position of the eye with respect to the target; and when the relative position of the eye corresponds to the target, automatically capture the at least one image of the fundus of the eye.

7 Claims, 19 Drawing Sheets

Related U.S. Application Data continuation of application No. 14/960,495, filed on Dec. 7, 2015, now Pat. No. 9,757,031, which is a continuation of application No. 14/177,594, filed on Feb. 11, 2014, now Pat. No. 9,237,847.

(51) Int. Cl.
*A61B 3/00* (2006.01)
*A61B 3/12* (2006.01)
*A61B 3/15* (2006.01)
*A61B 3/113* (2006.01)
*A61B 5/00* (2006.01)

(52) U.S. Cl.
CPC .......... *A61B 3/0041* (2013.01); *A61B 3/0091* (2013.01); *A61B 3/113* (2013.01); *A61B 3/14* (2013.01); *A61B 3/145* (2013.01); *A61B 3/152* (2013.01); *A61B 5/0013* (2013.01); *A61B 5/6803* (2013.01)

(58) Field of Classification Search
USPC ........................................................ 351/208
See application file for complete search history.

(56) References Cited

U.S. PATENT DOCUMENTS

| | | | |
|---|---|---|---|
| 5,599,276 A | 2/1997 | Hauptli et al. | |
| 5,703,621 A | 12/1997 | Martin et al. | |
| 5,713,047 A * | 1/1998 | Kohayakawa | A61B 3/12 351/206 |
| 5,776,060 A | 7/1998 | Smith et al. | |
| 5,784,148 A | 7/1998 | Heacock | |
| 5,943,116 A | 8/1999 | Zeimer | |
| 6,000,799 A | 12/1999 | Van de Velde | |
| 6,011,585 A | 1/2000 | Anderson | |
| 6,120,461 A | 9/2000 | Smyth | |
| 6,296,358 B1 | 10/2001 | Cornsweet et al. | |
| 6,301,440 B1 | 10/2001 | Bolle et al. | |
| 6,307,526 B1 | 10/2001 | Mann | |
| 6,309,070 B1 | 10/2001 | Svetliza et al. | |
| 6,325,511 B1 | 12/2001 | Mizuochi | |
| 6,350,031 B1 | 2/2002 | Lashkari et al. | |
| 6,556,853 B1 | 4/2003 | Cabib et al. | |
| 6,666,857 B2 | 12/2003 | Smith | |
| 7,134,754 B2 | 11/2006 | Kerr et al. | |
| 7,264,355 B2 | 9/2007 | Rathjen | |
| 7,284,859 B2 | 10/2007 | Ferguson | |
| 7,311,400 B2 | 12/2007 | Wakil et al. | |
| 7,364,297 B2 | 4/2008 | Goldfain et al. | |
| 7,380,938 B2 | 6/2008 | Chmielewski, Jr. et al. | |
| 7,387,384 B2 | 6/2008 | Heine et al. | |
| 7,404,640 B2 | 7/2008 | Ferguson et al. | |
| 7,470,024 B2 | 12/2008 | Chinaglia et al. | |
| 7,488,294 B2 | 2/2009 | Torch | |
| 7,502,639 B2 | 3/2009 | Kerr | |
| 7,568,628 B2 | 8/2009 | Wang et al. | |
| 7,611,060 B2 | 11/2009 | Wang et al. | |
| 7,621,636 B2 | 11/2009 | Su et al. | |
| 7,784,940 B2 | 8/2010 | Goldfain et al. | |
| 7,809,160 B2 | 10/2010 | Vertegaal et al. | |
| 7,871,164 B2 | 1/2011 | Luther et al. | |
| 7,926,945 B2 | 4/2011 | Dick et al. | |
| 7,963,653 B1 | 6/2011 | Ellman | |
| 7,976,162 B2 | 7/2011 | Flitcroft | |
| 8,109,634 B2 | 2/2012 | Gil | |
| 8,109,635 B2 | 2/2012 | Allon et al. | |
| 8,347,106 B2 | 1/2013 | Tsuria et al. | |
| 8,366,270 B2 | 2/2013 | Pujol Ramo et al. | |
| 8,388,523 B2 | 3/2013 | Vivenzio et al. | |
| 8,444,269 B1 | 5/2013 | Ellman | |
| 8,488,895 B2 | 7/2013 | Muller et al. | |
| 8,534,837 B2 | 9/2013 | Sayeram et al. | |
| 8,577,644 B1 | 11/2013 | Ksondzyk et al. | |
| 8,585,203 B2 | 11/2013 | Aikawa et al. | |
| 8,620,048 B2 | 12/2013 | Nakano et al. | |
| 8,649,008 B2 | 2/2014 | Kashani et al. | |
| 8,696,122 B2 | 4/2014 | Hammer et al. | |
| 8,714,743 B2 | 5/2014 | Verdooner | |
| 8,879,813 B1 | 11/2014 | Solanki et al. | |
| 9,211,064 B2 | 12/2015 | Wang | |
| 9,237,847 B2 | 1/2016 | Wang et al. | |
| 9,498,126 B2 | 11/2016 | Wang | |
| 9,757,031 B2 | 9/2017 | Wang et al. | |
| 9,918,629 B2 | 3/2018 | Wang | |
| 10,136,804 B2 | 11/2018 | Wang et al. | |
| 10,154,782 B2 | 12/2018 | Farchione et al. | |
| 10,159,409 B2 | 12/2018 | Wang et al. | |
| 2002/0101568 A1 | 8/2002 | Eberl et al. | |
| 2003/0009155 A1 | 1/2003 | Pawlowski et al. | |
| 2003/0071970 A1 | 4/2003 | Donnerhacke et al. | |
| 2003/0208125 A1 | 11/2003 | Watkins | |
| 2005/0012899 A1 | 1/2005 | Ferguson | |
| 2005/0043588 A1 | 2/2005 | Tsai | |
| 2005/0110949 A1 | 5/2005 | Goldfain et al. | |
| 2005/0254008 A1 | 11/2005 | Ferguson et al. | |
| 2006/0113386 A1 | 6/2006 | Olmstead | |
| 2006/0119858 A1 | 6/2006 | Knighton et al. | |
| 2006/0147095 A1 | 7/2006 | Usher et al. | |
| 2006/0202036 A1 | 9/2006 | Wang et al. | |
| 2006/0202038 A1 | 9/2006 | Wang et al. | |
| 2006/0268231 A1 | 11/2006 | Gil et al. | |
| 2007/0030450 A1 | 2/2007 | Liang et al. | |
| 2007/0174152 A1 | 7/2007 | Bjornberg et al. | |
| 2007/0188706 A1 | 8/2007 | Pearson et al. | |
| 2008/0084538 A1 | 4/2008 | Maeda et al. | |
| 2008/0165322 A1 | 7/2008 | Su et al. | |
| 2008/0231803 A1 | 9/2008 | Feldon et al. | |
| 2008/0316426 A1 | 12/2008 | Shibata et al. | |
| 2009/0096885 A1 | 4/2009 | Robinson et al. | |
| 2009/0225277 A1 | 9/2009 | Gil | |
| 2009/0275929 A1 | 11/2009 | Zickler | |
| 2009/0316115 A1 | 12/2009 | Itoh et al. | |
| 2009/0323022 A1 | 12/2009 | Uchida | |
| 2009/0323023 A1 | 12/2009 | Kogawa et al. | |
| 2010/0007849 A1 | 1/2010 | Liesfeld et al. | |
| 2010/0014052 A1 | 1/2010 | Koschmieder et al. | |
| 2010/0085538 A1 | 4/2010 | Masaki et al. | |
| 2010/0110375 A1 | 5/2010 | Nishio et al. | |
| 2010/0149489 A1 | 6/2010 | Kikawa et al. | |
| 2010/0208961 A1 | 8/2010 | Zahniser | |
| 2010/0238402 A1 | 9/2010 | Itoh et al. | |
| 2011/0001927 A1 | 1/2011 | Kasper | |
| 2011/0028513 A1 | 2/2011 | Zhuo et al. | |
| 2011/0043756 A1 | 2/2011 | Kahn et al. | |
| 2011/0169935 A1 | 7/2011 | Henriksen | |
| 2011/0234977 A1 | 9/2011 | Verdooner | |
| 2011/0242306 A1 | 10/2011 | Bressler et al. | |
| 2011/0261184 A1 | 10/2011 | Mason et al. | |
| 2011/0299034 A1 | 12/2011 | Walsh et al. | |
| 2011/0299036 A1 | 12/2011 | Goldenholz | |
| 2012/0002167 A1 | 1/2012 | Kondoh | |
| 2012/0044456 A1 | 2/2012 | Hayashi | |
| 2012/0050677 A1 | 3/2012 | Ohban | |
| 2012/0121158 A1 | 5/2012 | Sekine et al. | |
| 2012/0147327 A1 | 6/2012 | Shikaumi et al. | |
| 2012/0169995 A1 | 7/2012 | Mohr et al. | |
| 2012/0200690 A1 | 8/2012 | Beasley | |
| 2012/0213423 A1 | 8/2012 | Xu et al. | |
| 2012/0218301 A1 | 8/2012 | Miller | |
| 2012/0229617 A1 | 9/2012 | Yates et al. | |
| 2012/0229764 A1 | 9/2012 | Tomatsu et al. | |
| 2012/0248196 A1 | 10/2012 | Wang | |
| 2012/0249956 A1 | 10/2012 | Narasimha-Iyer et al. | |
| 2012/0257163 A1 | 10/2012 | Dyer et al. | |
| 2012/0281874 A1 | 11/2012 | Lure | |
| 2012/0320340 A1 | 12/2012 | Coleman, III | |
| 2013/0002711 A1 | 1/2013 | Sakagawa | |
| 2013/0010260 A1 | 1/2013 | Tumlinson et al. | |
| 2013/0016320 A1 | 1/2013 | Naba | |
| 2013/0033593 A1 | 2/2013 | Chinnock et al. | |
| 2013/0057828 A1 | 3/2013 | de Smet | |
| 2013/0063698 A1 | 3/2013 | Akiba et al. | |
| 2013/0128223 A1 | 5/2013 | Wood et al. | |

(56) References Cited

U.S. PATENT DOCUMENTS

| | | | |
|---|---|---|---|
| 2013/0162950 A1 | 6/2013 | Umekawa | |
| 2013/0169934 A1 | 7/2013 | Verdooner | |
| 2013/0176533 A1 | 7/2013 | Raffle et al. | |
| 2013/0194548 A1 | 8/2013 | Francis et al. | |
| 2013/0201449 A1 | 8/2013 | Walsh et al. | |
| 2013/0208241 A1 | 8/2013 | Lawson et al. | |
| 2013/0211285 A1 | 8/2013 | Fuller et al. | |
| 2013/0215387 A1 | 8/2013 | Makihira et al. | |
| 2013/0222763 A1 | 8/2013 | Bublitz et al. | |
| 2013/0229622 A1 | 9/2013 | Murase et al. | |
| 2013/0234930 A1 | 9/2013 | Palacios Goerger | |
| 2013/0250237 A1 | 9/2013 | Ueno | |
| 2013/0250242 A1 | 9/2013 | Cheng | |
| 2013/0301004 A1 | 11/2013 | Kahn et al. | |
| 2014/0022270 A1 | 1/2014 | Rice-Jones et al. | |
| 2014/0104573 A1 | 4/2014 | Iwanaga | |
| 2014/0111773 A1 | 4/2014 | Itoh | |
| 2014/0118693 A1 | 5/2014 | Matsuoka | |
| 2014/0118697 A1 | 5/2014 | Tanaka et al. | |
| 2014/0192320 A1 | 7/2014 | Tsao | |
| 2014/0198298 A1 | 7/2014 | Cheng et al. | |
| 2014/0204340 A1 | 7/2014 | Verdooner | |
| 2014/0204341 A1* | 7/2014 | Murase | A61B 3/102 351/208 |
| 2014/0211162 A1 | 7/2014 | Matsuoka et al. | |
| 2014/0268046 A1 | 9/2014 | Narasimha-Iyer et al. | |
| 2014/0330352 A1 | 11/2014 | Luttrull et al. | |
| 2015/0002811 A1 | 1/2015 | Ota | |
| 2015/0009357 A1 | 1/2015 | Seibel et al. | |
| 2015/0110348 A1 | 4/2015 | Solanki et al. | |
| 2015/0150449 A1 | 6/2015 | Matsumoto | |
| 2015/0170360 A1 | 6/2015 | Fletcher et al. | |
| 2015/0178946 A1 | 6/2015 | Krishnaswamy et al. | |
| 2015/0272434 A1 | 10/2015 | Satake et al. | |
| 2015/0342459 A1 | 12/2015 | Robert et al. | |
| 2016/0007845 A1* | 1/2016 | Utagawa | A61B 3/0025 351/206 |
| 2016/0058284 A1 | 3/2016 | Wang | |
| 2016/0092721 A1 | 3/2016 | Kanagasingam et al. | |
| 2016/0166141 A1 | 6/2016 | Kanagasingam et al. | |
| 2016/0188993 A1 | 6/2016 | Beato | |
| 2016/0213249 A1 | 7/2016 | Cornsweet et al. | |
| 2016/0249804 A1 | 9/2016 | Wang | |
| 2016/0287068 A1 | 10/2016 | Murase et al. | |
| 2016/0307341 A1 | 10/2016 | Sato et al. | |
| 2017/0020389 A1 | 1/2017 | Wang et al. | |
| 2017/0035292 A1 | 2/2017 | Wang | |
| 2017/0119241 A1 | 5/2017 | Farchione et al. | |
| 2017/0161892 A1 | 6/2017 | Tellatin et al. | |
| 2017/0172675 A1 | 6/2017 | Jarc et al. | |
| 2017/0181625 A1 | 6/2017 | Kawakami et al. | |
| 2017/0196452 A1 | 7/2017 | Wang | |
| 2017/0209044 A1 | 7/2017 | Ito et al. | |
| 2017/0239012 A1 | 8/2017 | Wood et al. | |
| 2017/0266041 A1 | 9/2017 | Kim et al. | |
| 2017/0311800 A1 | 11/2017 | Wang | |
| 2017/0316565 A1 | 11/2017 | Leahy et al. | |
| 2017/0332903 A1 | 11/2017 | Wang et al. | |
| 2018/0092530 A1 | 4/2018 | Hart et al. | |
| 2018/0140188 A1 | 5/2018 | Wang | |
| 2018/0263486 A1 | 9/2018 | Farchione et al. | |

FOREIGN PATENT DOCUMENTS

| | | |
|---|---|---|
| CN | 102917634 A | 2/2013 |
| CN | 205006859 U | 2/2016 |
| CN | 105433899 A | 3/2016 |
| CN | 205181314 U | 4/2016 |
| EP | 2 374 404 A1 | 10/2011 |
| EP | 2 425 763 A1 | 7/2012 |
| GB | 2378600 A | 12/2003 |
| JP | 2006-101943 A | 4/2006 |
| JP | 2009-172157 A | 8/2009 |
| JP | 2009-219644 A | 10/2009 |
| JP | 2010-57547 A | 3/2010 |
| JP | 2011-097992 A | 5/2011 |
| JP | 2012-213575 A | 11/2012 |
| JP | 2013-46850 A | 3/2013 |
| JP | 2013-59551 | 4/2013 |
| KR | 10-2013-0010079 | 1/2013 |
| WO | 2004/089214 A2 | 10/2004 |
| WO | 2006/016366 A2 | 2/2006 |
| WO | 2008/106802 A1 | 9/2008 |
| WO | 2010080576 A1 | 7/2010 |
| WO | 2010/115195 A1 | 10/2010 |
| WO | 2011/029064 A1 | 3/2011 |
| WO | 2012/009702 A1 | 1/2012 |
| WO | 2012134272 A1 | 10/2012 |
| WO | 2013/041658 A1 | 3/2013 |
| WO | 2013/082387 A1 | 6/2013 |
| WO | 2013/107464 A1 | 7/2013 |
| WO | 2014/182769 A1 | 11/2014 |
| WO | 2015/044366 A1 | 4/2015 |
| WO | 2015/170947 A1 | 11/2015 |

OTHER PUBLICATIONS

Dilating Eye Drops, AAPOS, http://web.archive.org/web/2012020409024/http://www.aapos.org/terms/conditions/43, Dilating Eye Drops, 2pgs, Dec. 17, 2015.

Muller et al., "Non-Mydriatic Confocal Retinal Imaging Using a Digital Light Projector," Ophthalmic Technologies XXIII, 2013, downloaded from: http://proceedings.spiedigitallibrary.org (8 pages).

Paques et al., "Panretinal, High-Resolution Color Photography of the Mouse Fundus," Investigative Ophthalmology & Visual Science, Jun. 2007, vol. 48, No. 6, pp. 2769-2774.

Spector,The Pupils, Clinical Methods: The History, Physical, and Laboratory Examinations, 3rd Edition, pp. 300-304, Chapter 58 (1990).

International Search Report and Written Opinion in PCT/US2015/015124 dated May 15, 2015, 10 pages.

Visucampro NM—The Non-Mydriatic Fundus Camera System from Carl Zeiss, Carl Zeiss Meditec, International, 2005 (1 page).

"A Portable, Scalable Retinal Imaging System," TI Engibous Competition Report (Spring 2012), Rice University, http://www.ti.com/corp/docs/university/docs/Rice_University_mobileVision%20Final%20Report.pdf (96 pages).

Girdwain, "Goggles Differentiate Between Stroke and Vertigo," Today's Geriatric Medicine, vol. 6 No. 4 p. 8, Today's GeriatricMedicine, Oct. 1, 2013, 2 pages.

Johns Hopkins Medicine, "Small Johns Hopkins-led study finds portable device diagnoses stroke with 100 percent accuracy," www.hopkinsmedicine.org/se/util/display_mod.cfm?MODULE=/se-server/mod/modules/semod_printpage/mod_default.cfm&PageURL-/news/media/releases/is_i . . . , Mar. 5, 2013, 2 pages.

Anastasakis et al., SLO-Infrared Imaging of the Macula and its Correlation with Functional Loss and Structural Changes in Patients with Stargardt Disease, May 1, 2012, 19 pgs.

Carrasco-Zevallos, O. et al., "Pupil Tracking Optical Coherence Tomography for Precise Control of Pupil Entry Position," Biomedical Optics Express: 6(9): 3405-3419, Sep. 1, 2015, 15 pgs.

EIDON—The First True Color Confocal Scanner on the Market, www.centervue.com, Jul. 27, 2015, 12 pgs.

Grieve et al., Multi-wavelength imaging with the adaptive optics scnaning laser Ophthalmoscope, Optics Express 12230, Dec. 11, 2006, vol. 14, No. 25, 13 pgs.

Hammer et al., Adaptive Optics Scanning Laser Ophthalmoscope for Stablized Retinal Imaging, Optics Express: 14(8): 3354-3367, Apr. 17, 2006, 14 pgs.

Markow et al., "Real-Time Algorithm for Retinal Tracking," IEEE Transactions on Biomedical Engineering; 40(12): 1269-1281, Dec. 1993, 13 pgs.

Moscaritolo et al., "A Machine Vision Method for Automated Alignment of Fundus Imaging Systems," Ophthalmic Surgery Lasers & Imaging: 41(6): 607-613, Sep. 29, 2010, 7 pgs.

Navilas, Navigated Laser Therapy—A New Era in Retinal Disease Management, www.od-os.com, © 2015, 16 pgs.

(56) References Cited

OTHER PUBLICATIONS

Sahin et al., "Adaptive Optics with Pupil Tracking for High Resolution Retinal Imaging," Biomedical Optics Express: 3(2): 225-239, Feb. 1, 2012, 15 pgs.
Sheehy et al., "High-speed, Image-based eye tracking with a scanning laser ophthalmoscope," Biomedical Optics Express; 3(10): 2611-2622, Oct. 1, 2012, 12 pgs.
Land, Edwin H., "The Retinex Theory of Color Visison," Scientific America, Dec. 1977, vol. 237 No. 6 p. 108-128.
Mayer et al., "Wavelet denoising of multiframe optical coherence tomography data," Biomedical Optics Express, vol. 3, No. 3, pp. 572-589 (Mar. 1, 2012).
U.S. Appl. No. 15/980,498, filed May 15, 2018.
User Manual Non-Mydriatic Retinal Camera, Topcon Corporation, Tokyo, Japan, 106 pages (2014).

\* cited by examiner

OPTHALMOSCOPE DEVICE

CROSS REFERENCE TO RELATED APPLICATION

This application is a continuation of U.S. patent application Ser. No.: 15/662,363 filed Jul. 28, 2018, Now U.S. Pat. No. 10,159,409 B2, continuation of U.S. patent application Ser. No.: 14/960,495 filed Dec. 7, 2015; Now U.S. Pat. No. 9,757,031 B2; continuation of Ser. No. 14/177,594 filed on Feb. 11, 2014; Now U.S. Pat. No. 9,237,847 B2

BACKGROUND

An ophthalmoscope is device used to image the fundus (or eye fundus) and other structures of the eye. This imaging is used to determine the health of the retina and vitreous humor and to evaluate conditions such as hypertension, diabetic retinopathy, and papilledema. The ophthalmoscope device may include a camera that is used to capture the images and a display used to display the images obtained by the ophthalmoscope device. The eye must be aligned properly with the device to capture fundus images.

Typically the ophthalmoscope is a hand-held device or a headband-mounted device that is worn by a caregiver.

SUMMARY

In one aspect, a wearable device configured to capture eye fundus images comprises: a support structure configured to be worn by a subject; a display device coupled to the support structure, the display device configured to overlay an overlay image in a field of view of the subject; and an image capture device coupled to the support structure, the image capture device configured to capture images of an eye fundus of the subject.

In another aspect, a wearable device configured to capture eye fundus images comprises: a support structure configured to be worn by a subject; a display device coupled to the support structure, the display device configured to overlay an overlay image in a field of view of the subject, the display device comprising: a projector configured to project a pattern of light representing the overlay image; and a prism disposed in the field of view of the subject, the prism configured to direct at least a portion of the pattern of light towards an eye fundus of the subject; an image capture device coupled to the support structure, the image capture device configured to capture images of the eye fundus through the prism of the display device; and a control module programmed to: instruct the image capture device to capture a plurality of images in a first image capture mode; process at least a portion of the plurality of images to determine a position of a pupil of the subject; and instruct the image capture device to capture an image in a second image capture mode when the position of the pupil is substantially aligned with an optical axis of the image capture device, wherein: the first image capture mode comprises a first resolution and a first illumination condition; the second image capture mode comprises a second resolution and a second illumination condition; the second resolution is greater than or equal to the first resolution; and the second illumination condition is brighter than the first illumination condition.

In yet another aspect, a method for capturing an eye fundus image of a subject using a wearable ophthalmoscope, comprises: securing the wearable ophthalmoscope to the subject; capturing a plurality of images, by the wearable ophthalmoscope, of a pupil of the subject, wherein the plurality of images are captured in a first image capture mode; processing at least a portion of the plurality of images to determine a position of the pupil; and capturing an eye fundus image of the subject when the position of the pupil is in a desired position, wherein the eye fundus image is captured in a second image capture mode.

DETAILED DESCRIPTION

The present disclosure relates to an ophthalmoscope device and methods for capturing images from ophthalmoscope devices. In some embodiments, the ophthalmoscope device is worn by the subject of the images. In other embodiments, the ophthalmoscope device is held by a caregiver. The ophthalmoscope device captures images of the fundus (or eye fundus) of the subject through the subject's pupil. Often the fundus images include the fovea. The ophthalmoscope device captures these images when the subject's eye is oriented to provide a line of site through the pupil to the fundus and fovea.

Figure 1:
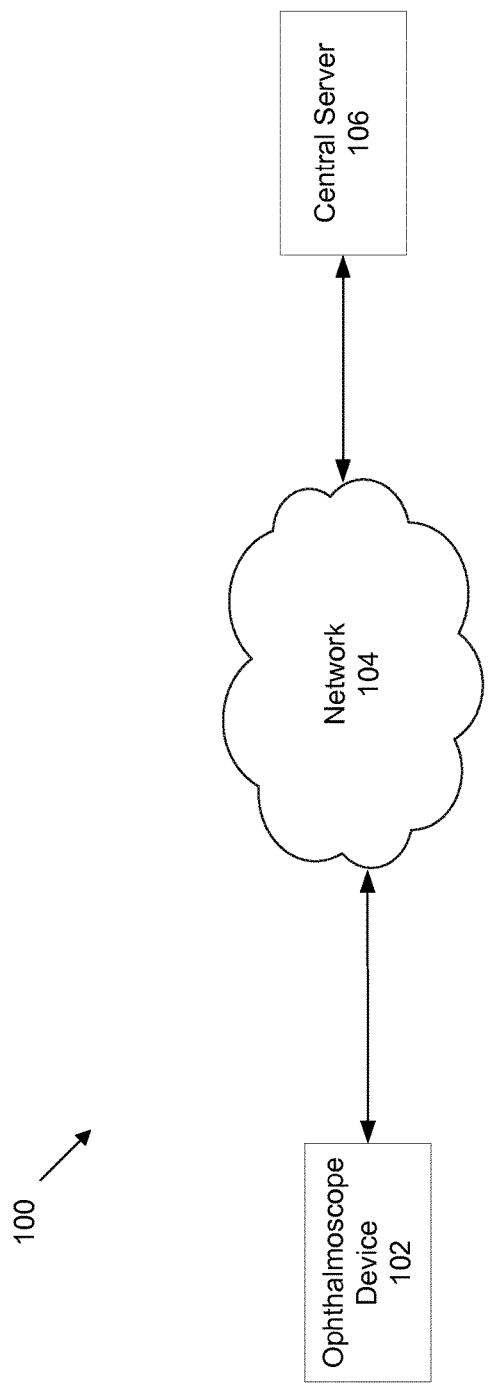
FIG. 1 shows an example system for performing ophthalmoscopy procedures.

FIG. 1 is an example system 100 for performing ophthalmoscopy procedures. In this example, an ophthalmoscope device 102 is configured to be worn by a subject or wearer and to capture eye fundus images of that subject. In other examples, the ophthalmoscope device 102 is configured to be held by the hand of a caregiver. In some embodiments, the ophthalmoscope device 102 is used to capture digital images. In other embodiments, the ophthalmoscope device 102 is used to capture film images.

In addition, in some embodiments, the ophthalmoscope device 102 is configured to send data associated with the digital images to a central server 106. For example, the ophthalmoscope device 102 can be programmed to send digital images to the central server 106 for additional processing and/or storage in an electronic medical record (EMR).

The ophthalmoscope device 102 and the central server 106 communicate through a network 104. In one example, the ophthalmoscope device 102 and network 104 are part of a CONNEX™ system from Welch Allyn of Skaneateles Falls, N.Y., although other systems can be used. In such an example, the monitor devices communicate through known protocols, such as the Welch Allyn Communications Protocol (WACP). WACP uses a taxonomy as a mechanism to define information and messaging. Taxonomy can be defined as description, identification, and classification of a semantic model. Taxonomy as applied to a classification scheme may be extensible. Semantic class-based modeling utilizing taxonomy can minimize the complexity of data description management by limiting, categorizing, and logically grouping information management and operational functions into families that contain both static and dynamic elements.

In another example, the central server 106 can be a distributed network, commonly referred to as a "cloud" server. The ophthalmoscope device 102 communicates with the cloud server through non-proprietary, industry standard messaging. Data encryption is also based on industry standards.

The network 104 is an electronic communication network that facilitates communication between the ophthalmoscope device 102 and the central server 106. An electronic communication network is a set of computing devices and links between the computing devices. The computing devices in the network use the links to enable communication among the computing devices in the network. The network 104 can include routers, switches, mobile access points, bridges, hubs, intrusion detection devices, storage devices, stand-alone server devices, blade server devices, sensors, desktop computers, firewall devices, laptop computers, handheld computers, mobile telephones, and other types of computing devices.

In various embodiments, the network 104 includes various types of links. For example, the network 104 can include wired and/or wireless links, including Bluetooth, ultra-wideband (UWB), 802.11, ZigBee, and other types of wireless links. Furthermore, in various embodiments, the network 104 is implemented at various scales. For example, the network 104 can be implemented as one or more local area networks (LANs), metropolitan area networks, subnets, wide area networks (such as the Internet), or can be implemented at another scale. Additionally, the network 104 includes networks formed between the ophthalmoscope device 102 and a peripheral device using a wireless network protocol (e.g., a mouse connected using Bluetooth, etc.).

The ophthalmoscope device 102 and the central server 106 are computing devices. A computing device is a physical, tangible device that processes data. Example types of computing devices include personal computers, standalone server computers, blade server computers, mainframe computers, handheld computers, smart phones, special purpose computing devices, and other types of devices that process data.

Computing devices can include at least one central processing unit ("CPU"), a system memory, and a system bus that couples the system memory to the CPU. The system memory includes a random access memory ("RAM") and a read-only memory ("ROM"). A basic input/output system containing the basic routines that help to transfer information between elements within the device, such as during startup, is stored in the ROM. The device further includes a mass storage device. The mass storage device is able to store software instructions and data.

The mass storage device and its associated computer-readable data storage media provide non-volatile, non-transitory storage for the device. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the device.

The computing device can also include an input/output controller for receiving and processing input from a number of other devices, including a keyboard, a mouse, a touch user interface display screen, or another type of input device. Similarly, the input/output controller provides output to a touch user interface display screen, a printer, or other type of output device.

Figure 2:
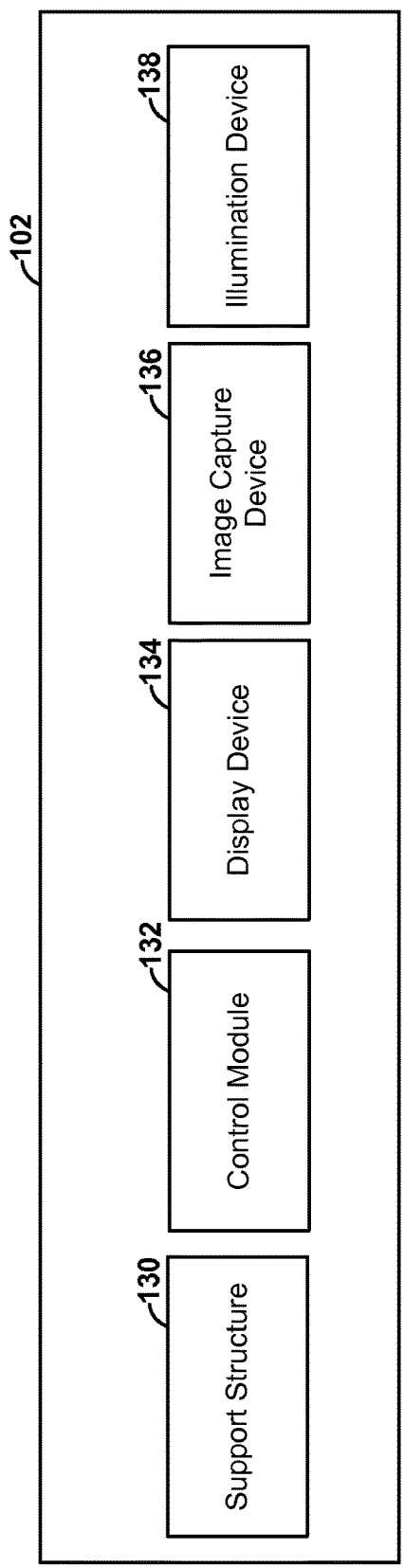
FIG. 2 shows an example ophthalmoscope device of the system of FIG. 1.

Referring now to FIG. 2, the ophthalmoscope device 102 is shown in more detail. In this example, the ophthalmoscope device 102 includes a support structure 130, a control module 132, a display device 134, an image capture device 136, and an illumination device 138.

The support structure 130 is a physical structure that holds the other components of the ophthalmoscope device 102 and, in some embodiments, is configured to couple to the wearer. In some embodiments, the support structure 130 is an eye glasses frame. In other embodiments, the support structure 130 is a headband. In some embodiments, the support structure 130 is formed from a rigid material, such as some plastics, metals, or composites. In other embodiments, the support structure 130 is formed from a semi-rigid or flexible material, such as rubber, elastic, or some plastics. In yet other embodiments, the support structure 130 is formed from a combination of materials, including rigid materials, semi-rigid materials, and flexible materials. Other embodiments of the support structure 130 are possible as well. Although the support structure 130 described in this embodiment is configured to be coupled to the wearer, in other embodiments the support structure 130 is configured to be held in a hand of a caregiver. The support structure 130 is an example of a housing.

The control module 132 is a module configured to control the operation of the ophthalmoscope device 102. The control module 132 can include a computing device. In some embodiments, the control module 132 controls the operation of the display device 134, the image capture device 136, and the illumination device 138.

The display device 134 is a device configured to display images or patterns of light that are visible to the wearer of the ophthalmoscope device 102. The display device 134 is shown and described in greater detail with respect to FIGS. 3-8. In some embodiments, the display device 134 is the display included in Google Glass from Google Inc. of Mountain View, Calif.

The image capture device 136 is a device configured to capture images of the wearer of the ophthalmoscope device 102. In some embodiments, the image capture device 136 includes a camera or image capture sensor, such as a charge-coupled device or complementary metal-oxide-semiconductor. In some embodiments, the image capture device 136 includes a digital video camera. Yet other embodiments of the image capture device 136 are possible as well. In the examples shown, the image that is captured is a digital image. In the example shown, the image capture devices can capture images in a variety of formats, such as JPEG, BITMAP, TIFF, etc. The image capture device 136 is shown and described in greater detail with respect to FIGS. 3 and 6-10.

The illumination device 138 is a device configured to generate and direct light towards the eye of the wearer of the ophthalmoscope device 102 so that the structures of the eye may be imaged. In some embodiments, the illumination device 138 comprises one or more light emitting diodes, incandescent bulbs, or fiber optic cables. Yet other embodiments of the illumination device 138 are possible as well. In some embodiments, the illumination device 138 is configured to create multiple illumination conditions, each having a different intensity (i.e., brightness) of light. However, some embodiments of the ophthalmoscope device 102 do not include an illumination device 138.

Figure 3:
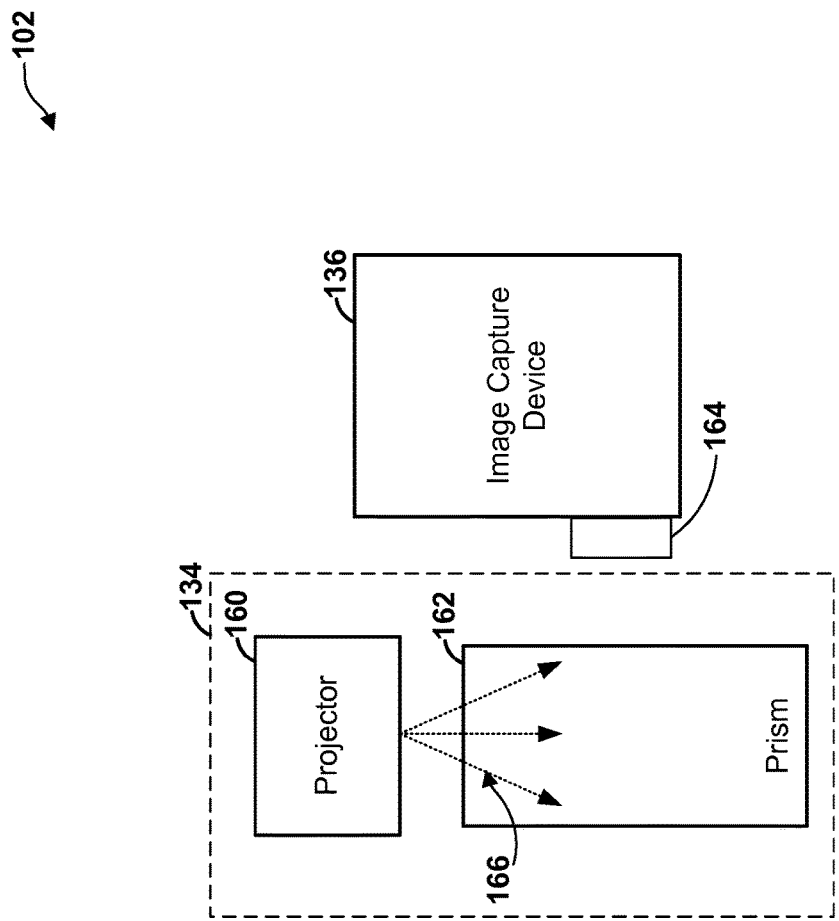
FIG. 3 shows an example display device and image capture device of the ophthalmoscope device of FIG. 2.

Referring now to FIG. 3, embodiments of the display device 134 and the image capture device 136 of the ophthalmoscope device 102 are shown in more detail. The display device 134 includes a projector 160 and a prism 162. The image capture device includes a lens 164. Also shown are projected light rays 166.

The projector 160 is an optical device that projects images or light. In some embodiments, the projector 160 receives electronic signals corresponding to images and projects patterns of light corresponding to those images. In the embodiment shown, the projector projects images or light through a surface of the prism 162.

The prism 162 is an optical element and is configured to refract light rays that enter through one of its surfaces out through a different surface. In the embodiment shown, the prism 162 refracts the projected light rays 166 projected by the projector by approximately ninety degrees. In some embodiments, the prism 162 is transparent or semi-transparent.

The lens 164 is an optical device that transmits and directs light rays from outside the image capture device 136 into the image capture device 136. In the embodiment shown, the lens 164 is disposed to receive light rays that pass through the prism 162.

Figure 4:
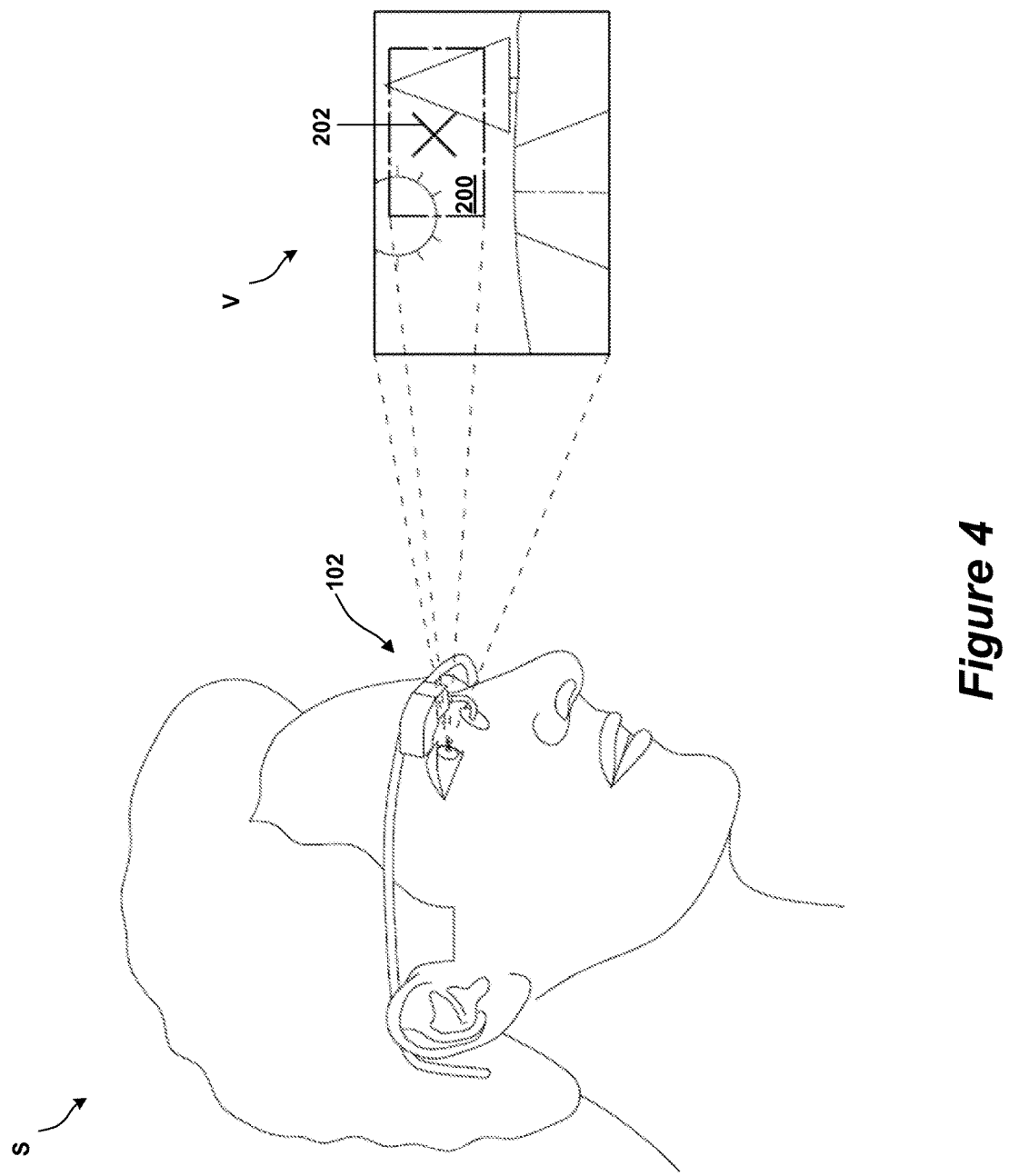
FIG. 4 shows an example of a subject wearing an example of the ophthalmic device of FIG. 2.

Referring now to FIG. 4, an illustration of a subject S wearing an embodiment of the ophthalmoscope device 102 is shown. Also shown is the field of view V of the subject S.

In the embodiment shown, the subject S is wearing the ophthalmoscope device 102 like a pair of glasses. The device rests on the bridge of the nose of the subject S and includes arms that wrap around the head of the subject S. In some embodiments, the arms rest on the ears of the subject S.

The field of view V illustrates an overlay layer 200. The overlay layer 200 corresponds to the portion of the field of view V in which the display device 134 may overlay images. In the example shown an image of a cursor 202 is displayed in the field of view V of the subject S on the overlay layer 200. In some embodiments, the overlay layer 200 is transparent or translucent. Accordingly, on portions of the overlay layer 200 that are not displaying an image, the field of view V of the subject S is not occluded. In some embodiments, the overlay layer 200 is not transparent or translucent and the field of view V of the subject S is occluded even when images are not being displayed. Additionally, in some embodiments, the image capture device 136 (not shown in this figure) occludes the field of view V of the subject S even when the overlay layer 200 is transparent or translucent. In some embodiments, the overlay layer 200 is the same size as the field of view V.

Figure 5:
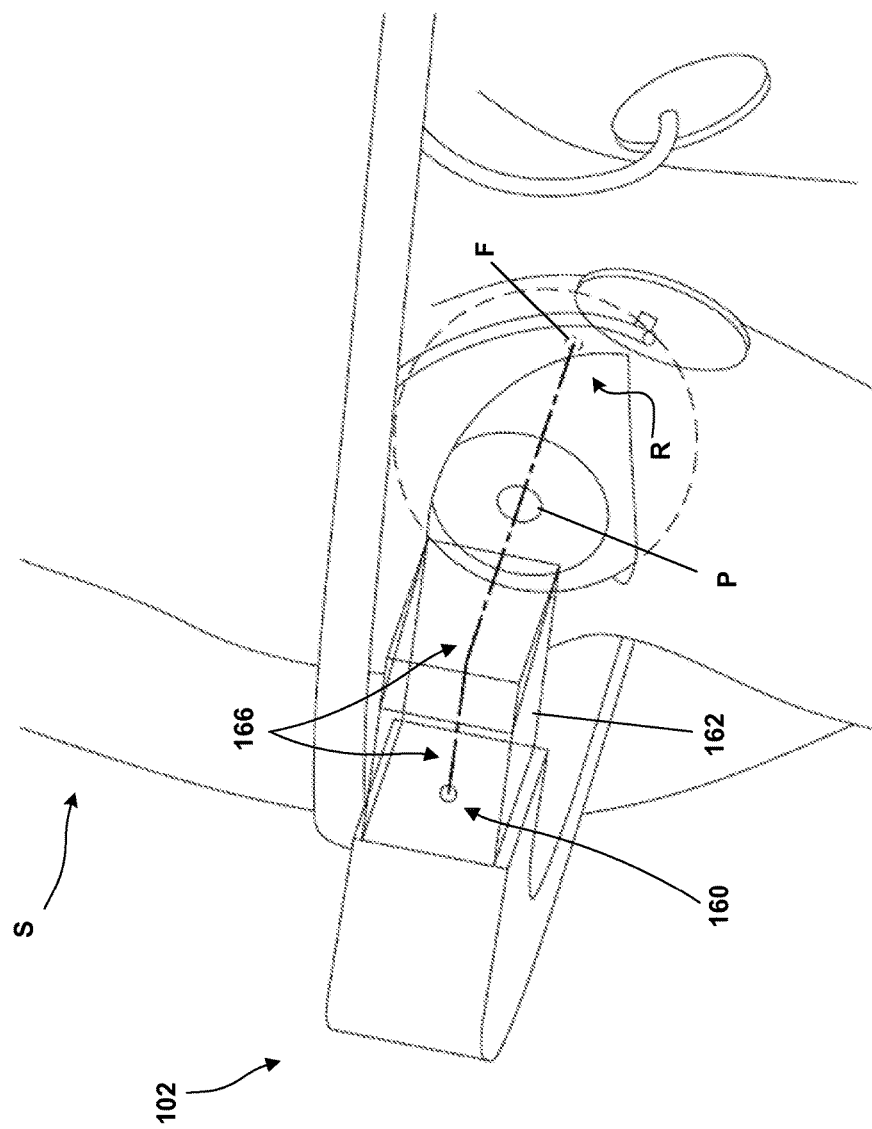
FIG. 5 shows another example of a subject wearing an example of the ophthalmic device of FIG. 2.

Referring now to FIG. 5, a front-view illustration of a subject S wearing an embodiment of the ophthalmoscope device 102 is shown. As shown in this figure, the projected light rays 166 are refracted by the prism 162. After being refracted, the projected light rays 166 pass through the pupil P of the subject S and contact the retina R of the subject S. If the subject S is focusing on the image being projected by the projector 160, the eye of the subject S will be oriented such that the projected light rays 166 will contact the fovea F of the subject S. The fovea F is the region of the retina R where vision is are sharpest. It is located in the center of the macula region of the retina R.

Figure 6:
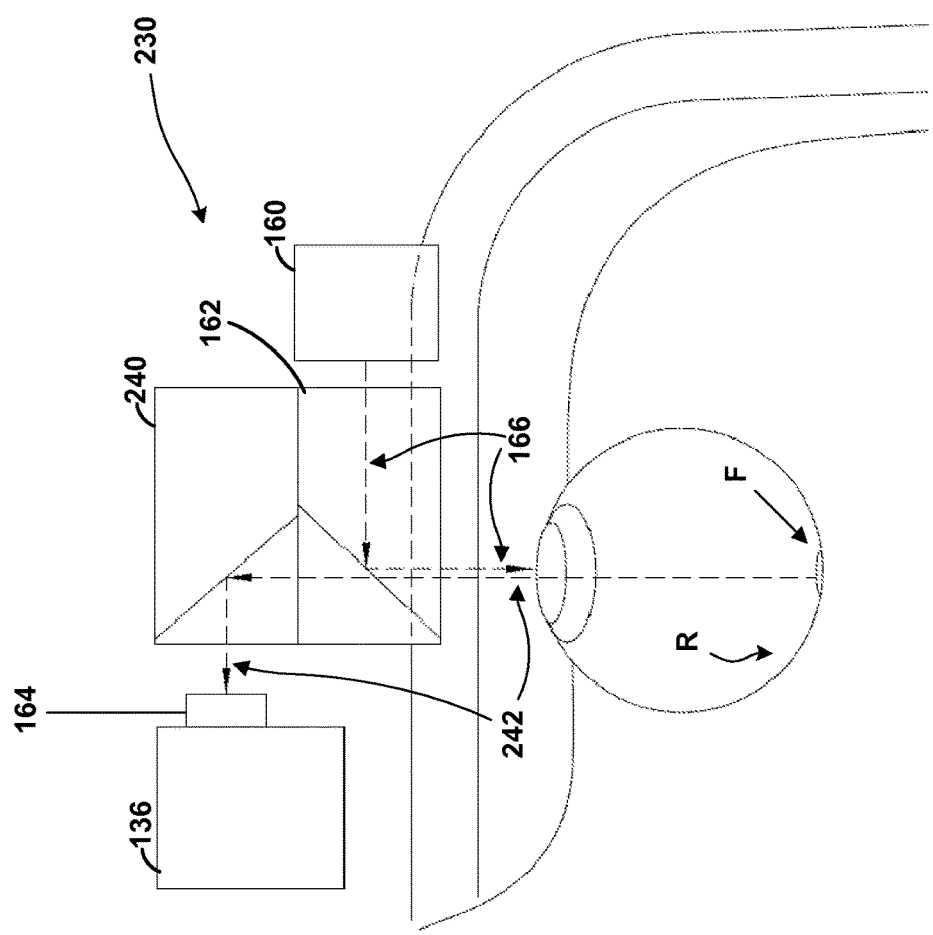
FIG. 6 shows an example of a subject wearing another embodiment of the ophthalmic device of the system of FIG. 1.

Referring now to FIG. 6, a top-view illustration of a subject S wearing another embodiment of the ophthalmoscope device 230 is shown. In this illustration, the image capture device 136, lens 164, reflection device 240, and image light rays 242 are shown. The ophthalmoscope device 230 is similar to the ophthalmoscope device 102 except that it includes the reflection device 240 and the image capture device 136 is disposed on a side of that reflection device 240.

The reflection device 240 is an optical device and is configured to direct the image light rays 242 into the lens 164 of the image capture device 136. In some embodiments, the reflection device 240 is a prism. In other embodiments, the reflection device 240 is a mirror. Other embodiments of the reflection device 240 are possible as well.

The image light rays 242 are light rays that are reflected by the various eye structures. At least a portion of the image light rays 242 are captured by the image capture device 136 to generate an image.

Although in the embodiment shown in FIG. 6, the image capture device 136 is disposed on the opposite side of the reflection device 240 from the projector 160, in other embodiments, the image capture device 136 is disposed in other locations, such as next to the projector 160.

Figure 7:
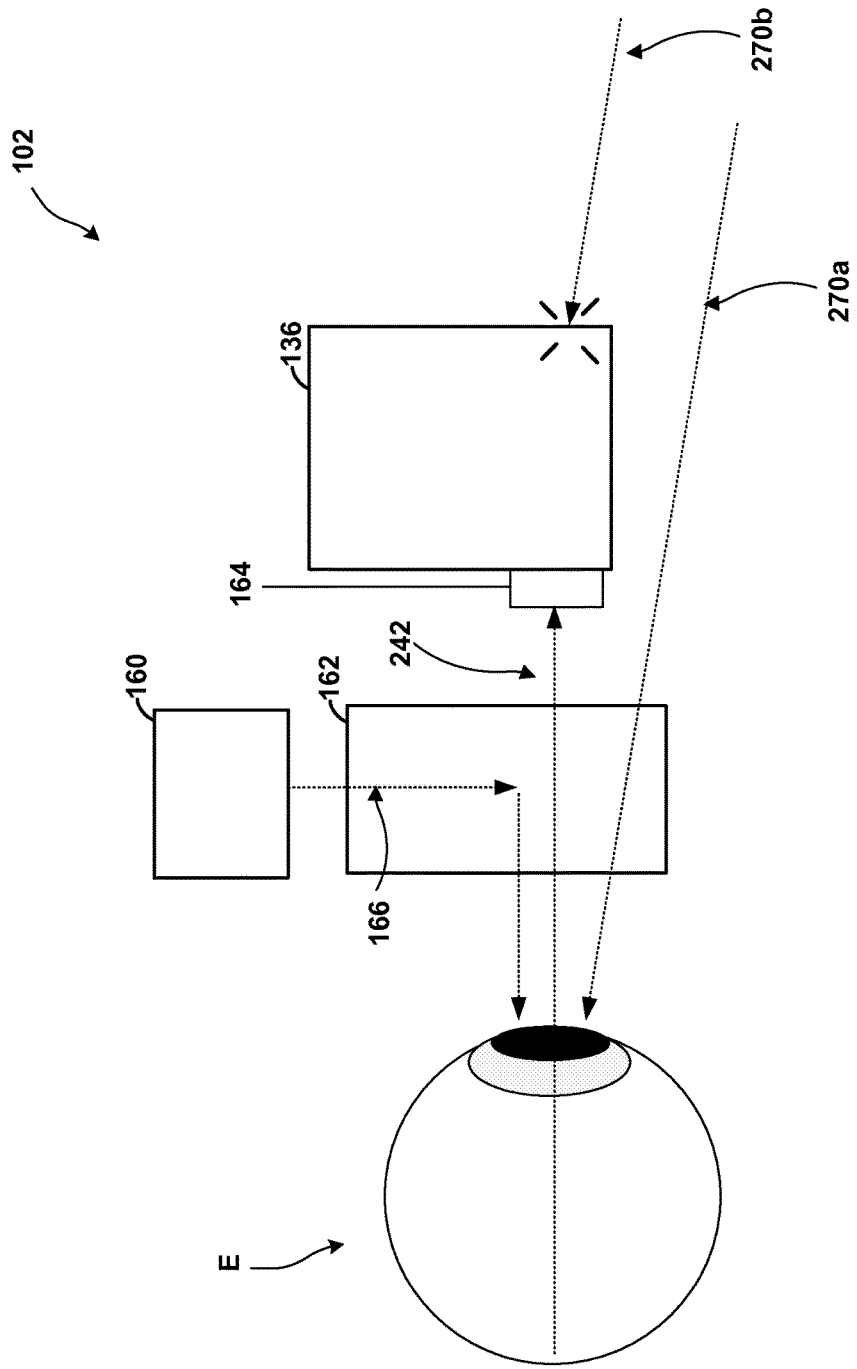
FIG. 7 shows an example of the ophthalmic device of FIG. 2 and an eye of a subject.

Referring now to FIG. 7, a top-view illustration of an embodiment of the ophthalmoscope device 102 and an eye E of a subject S. Also shown are projected light rays 166, image light rays 242, and environment light rays 270a-b. The environment light rays 270a-b include light rays from ambient light sources.

The projector 160 is configured to project projected light rays 166 into the prism 162, where the projected light rays 166 are refracted towards the eye E. Because the projector 160 is disposed on the side of the prism 162, it does not occlude the subject's view significantly.

The image capture device 136 is disposed across the prism 162 from the eye E. The lens 164 is configured to image the eye E through the prism 162. The lens 164 transmits image light rays 242 into the image capture device 136 for imaging. The image light rays 242 pass are reflected by the eye E and pass through the prism 162 to reach the lens 164. The image light rays 242 pass through the prism 162.

Additionally, some of the environment light rays 270a-b also reach the eye E. In this manner, the subject can perceive the environment while also perceiving the projected light rays 166. However, only some of the environment light rays 270a-b reach the eye E, because the image capture device 136 occludes the subjects field of view. For example, environment light ray 270a is not occluded by the image capture device 136 and reaches the eye E. Conversely, environment light ray 270b is occluded by the image capture device 136 and does not reach the eye E. In some embodiments, the environment light rays 270a-b are occluded to reduce the chance of glare.

Figure 8:
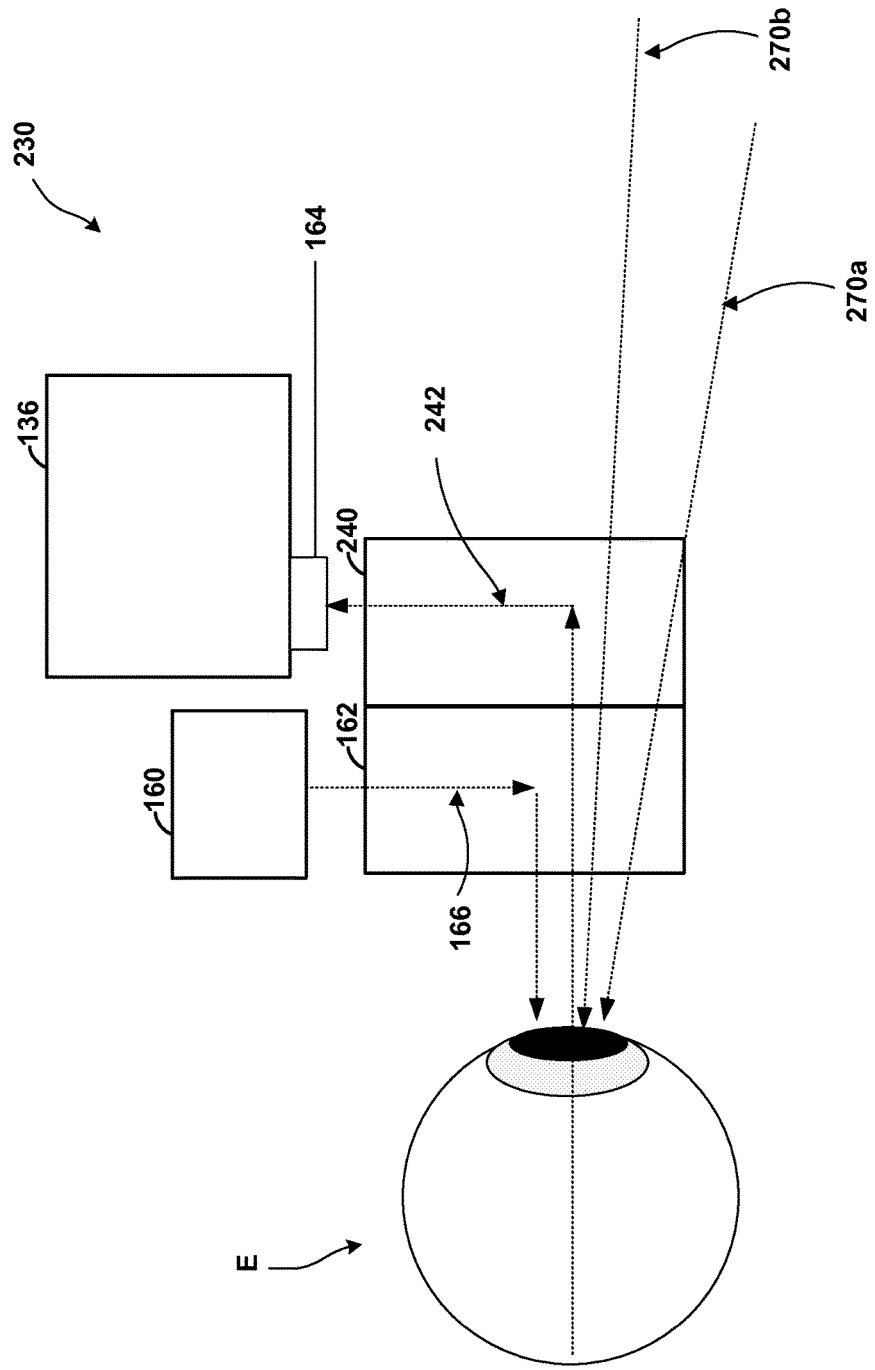
FIG. 8 shows an example of the ophthalmic device of FIG. 6 and an eye of a subject.

Referring now to FIG. 8, another top-view illustration of an embodiment of the ophthalmoscope device 230 and an eye E of a subject S. Also shown are projected light rays 166, image light rays 242, and environment light rays 270a-b.

Although the image light rays 242 pass through the prism 162 without being refracted significantly, the image light rays 242 are refracted by the reflection device 240. In this manner, the image light rays 242 are redirected by the reflection device 240 into the lens 164 for imaging by the image capture device 136.

In this embodiment, neither the projector 160 nor the image capture device 136 significantly occlude the field of view of the subject S. Further, the embodiment of reflection device 240 shown allows at least a portion of the light proximate to the subject to reach the eye E. As shown, both of the environment light rays 270a and 270b reach the eye E.

Figure 9:
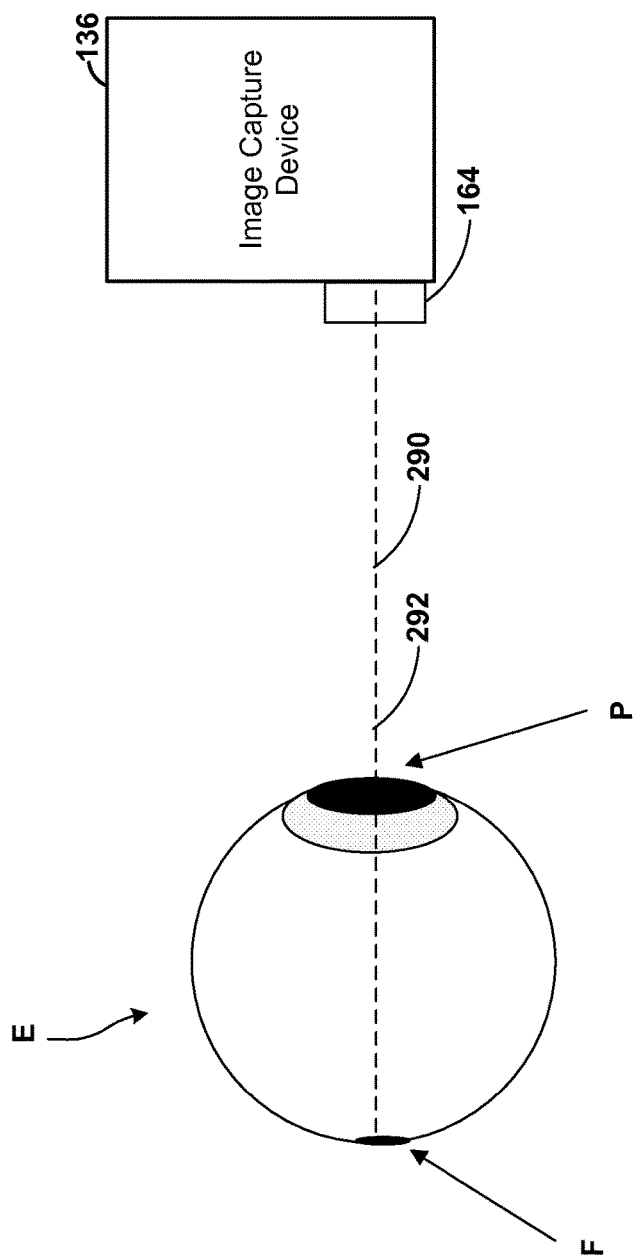
FIG. 9 shows an example of the image capture device of FIG. 3 and the eye of a subject.

Referring now to FIG. 9, a top view illustration of an arrangement of an embodiment of the image capture device 136 and an eye E of a subject S is shown. Also shown are the optical axis 290 of the image capture device 136 and the pupil/fovea orientation axis 292.

In the arrangement shown, the pupil/fovea orientation axis 292 is aligned with the optical axis 290 of the image capture device 136. Accordingly, in this arrangement, the image capture device 136 can capture a fundus image that includes the fovea F, which is often desired.

The optical axis 290 of the image capture device 136 is not a physical structure, but instead refers to the axis about which the image capture device 136 receives optical information. Generally, the optical axis 290 runs through the center of the lens 164 and is perpendicular to the surface at the center of the lens 164. In embodiments where the image capture device 136 is configured to capture image light rays 242 that have been refracted by the reflection device 240, the optical axis 290 is also refracted similarly.

The pupil/fovea orientation axis 292 is not a physical structure, but instead refers to an axis formed between the fovea F and the pupil P of the eye E. It corresponds to the orientation of the eye E.

Figure 10:
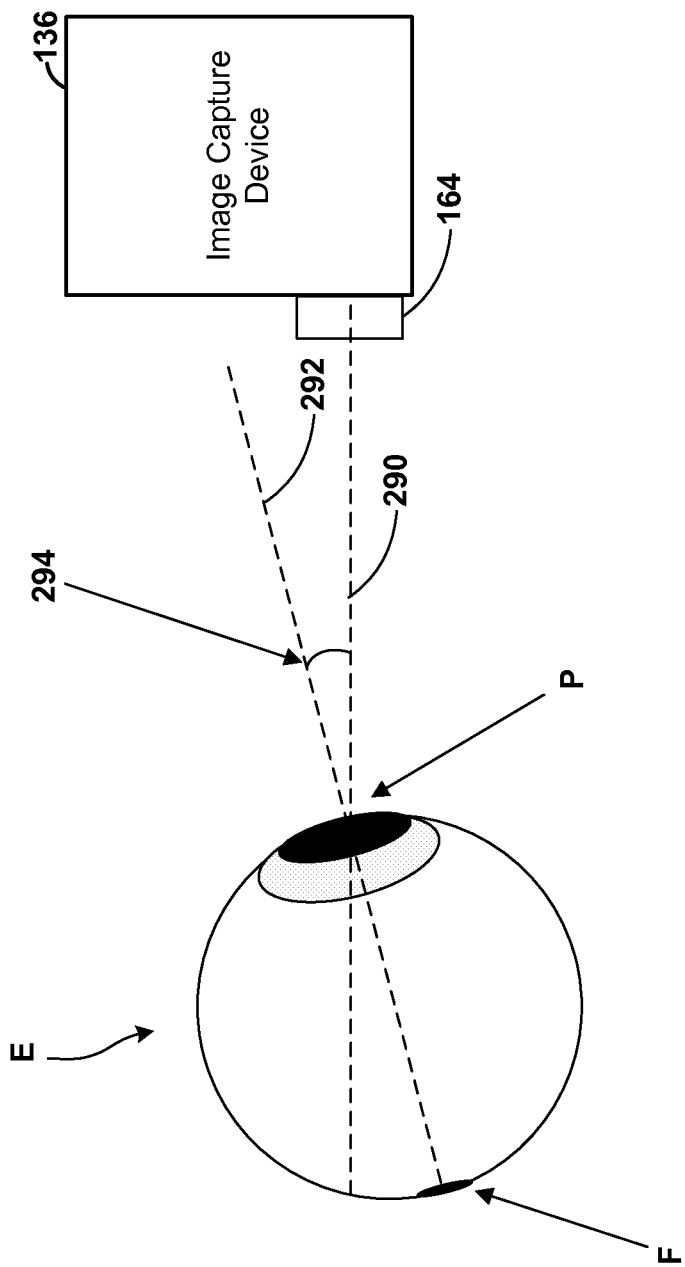
FIG. 10 shows another example of the image capture device of FIG. 3 and the eye of a subject.

Referring now to FIG. 10, a top view illustration of an arrangement of an embodiment of the image capture device 136 and an eye E of a subject S is shown. Also shown are the optical axis 290 of the image capture device 136, the pupil/fovea orientation axis 292, and the angle 294.

In the arrangement shown, the angle 294 represents the difference between the pupil/fovea orientation axis 292 and the optical axis 290. In some embodiments, if angle 294 is less than 2-15 degrees, the optical axis 290 and the pupil/fovea orientation axis 292 are considered substantially aligned. In other embodiments, optical axis 290 and the pupil/fovea orientation axis 292 are compared to a larger or smaller angle to determine whether they are substantially aligned. In these embodiments, the image capture device 136 may capture a fundus image if the optical axis 290 and the pupil/fovea orientation axis 292 are determined to be substantially aligned.

In other embodiments, the image capture device 136 may capture a fundus image if the position of the pupil P is substantially aligned with an optical axis 290. In some embodiments, the pupil P is considered to be substantially aligned with the optical axis 290 when the optical axis 290 crosses the pupil P. In some embodiments, the illumination level detected by the image capture device 136 is used to determine whether the optical axis 290 is aligned with the pupil P and whether the image capture device 136 is able to see through the pupil P. In some embodiments, at least a portion of the images captured by the image capture device are processed by an automatic thresholding algorithm, such as Otsu's method, to binomially separate the image into regions based on illumination levels. The resulting binomially separated regions or the histogram of detected illumination levels can then be used to determine whether the image capture device 136 is seeing through the pupil P to the fundus.

In some embodiments, if the pupil/fovea orientation axis 292 is not substantially aligned with the optical axis 290 of the image capture device 136, the angle 294 is measured and used to guide the eye E to a desired orientation for fundus imaging.

Figure 11:
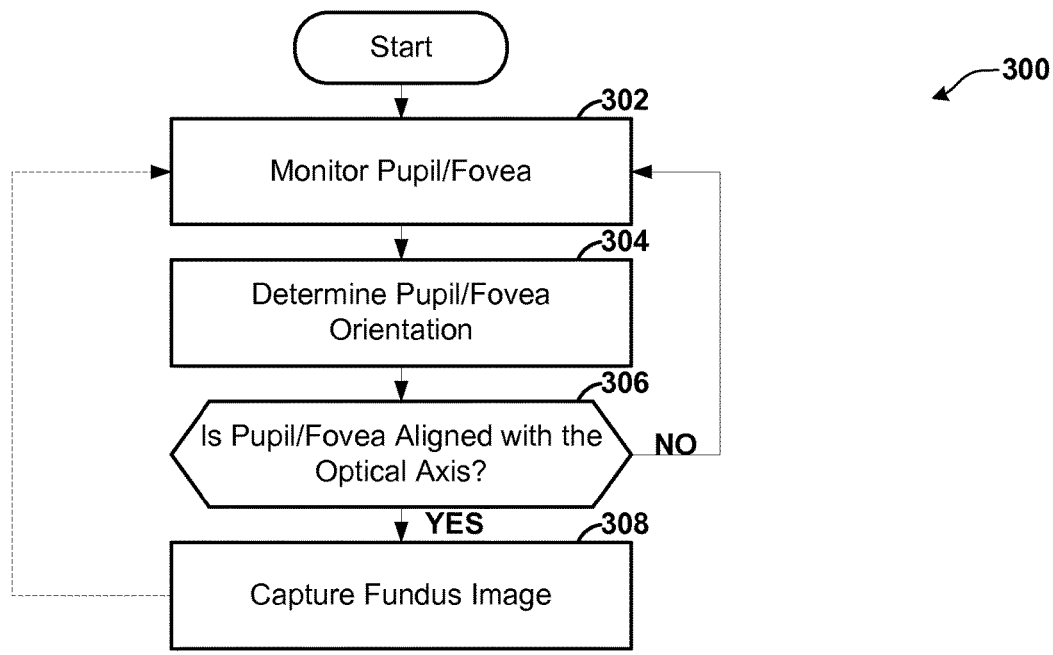
FIG. 11 shows an example process of capturing eye fundus images with the system of FIG. 1.

Referring now to FIG. 11, a process 300 performed using some embodiments of the ophthalmoscope device 102 is shown. The process 300 operates to image the fundus of the subject S using passive eye tracking. In the process 300, the ophthalmoscope device 102 monitors the pupil/fovea orientation of the subject S. Although the process 300 is described with respect to ophthalmoscope device 102, the process 300 may be performed using a wearable or nonwearable ophthalmoscope, such as a handheld digital ophthalmoscope.

Initially, at step 302, the pupil or fovea or both of the subject S are monitored. The image capture device 136 captures images in a first image capture mode. In the first image capture mode, the image capture device 136 captures images at a higher frame rate. In some embodiments, in the first image capture mode, the image capture device 136 captures images with lower illumination and at lower resolutions. In some embodiments, the lower illumination is created by the illumination device 138 operating to generate and direct light of a lower intensity towards the subject. In other embodiments, the lower illumination is created by an external light source or ambient light. Additionally, in other embodiments, the lower illumination is created by the display device 134. The first image capture mode may minimize discomfort to the subject S, allow the subject S to relax, and allow for a larger pupil size without dilation (non-mydriatic).

Next, at step 304, the control module 132 processes at least a portion of the images captured by the image capture device 136. The control module 132 processes the images to identify the location of the pupil or fovea or both of the subject S. Using the location of the pupil or fovea or both in one of the images, a vector corresponding to the pupil/fovea orientation is calculated. In some embodiments, the pupil/fovea orientation is approximated based on the distance between the pupil and fovea in the image. In other embodiments, the pupil/fovea orientation is calculated by approximating the position of the fovea relative to the pupil in three dimensions using estimates of the distance to the pupil and the distance between the pupil and the fovea. In other embodiments, the pupil/fovea orientation is approximated from the position of the pupil alone. In yet other embodiments, other methods of approximating the pupil/fovea orientation are used.

Next, at step 306, the pupil/fovea orientation is compared to the optical axis of the image capture device 136. If the pupil/fovea orientation is substantially aligned with the optical axis of the image capture device 136, the process proceeds to step 308 to capture a fundus image. If not, the process returns to step 302 to continue to monitor the pupil or fovea. In some embodiments, the pupil/fovea orientation is substantially aligned with the optical axis when the angle between them is less than two to fifteen degrees.

Next, at step 308, a fundus image is captured. In some embodiments, the fundus image is captured in a second image capture mode. In some embodiments, in the second image capture mode, the image capture device 136 captures images with higher illumination and at higher resolutions. In some embodiments, the higher illumination is created by the illumination device 138 operating to generate and direct light of a higher intensity towards the subject. In other embodiments, the higher illumination is created by an external light source or ambient light. Additionally, in other embodiments, the higher illumination is created by the display device 134. The second image capture mode may facilitate capturing a clear, well-illuminated, and detailed fundus image.

In some embodiments, after step 308, the process 300 returns to step 302 to continue to monitor the pupil/fovea orientation. The process 300 may continue to collect fundus images indefinitely or until a specified number of images have been collected.

Figure 12:
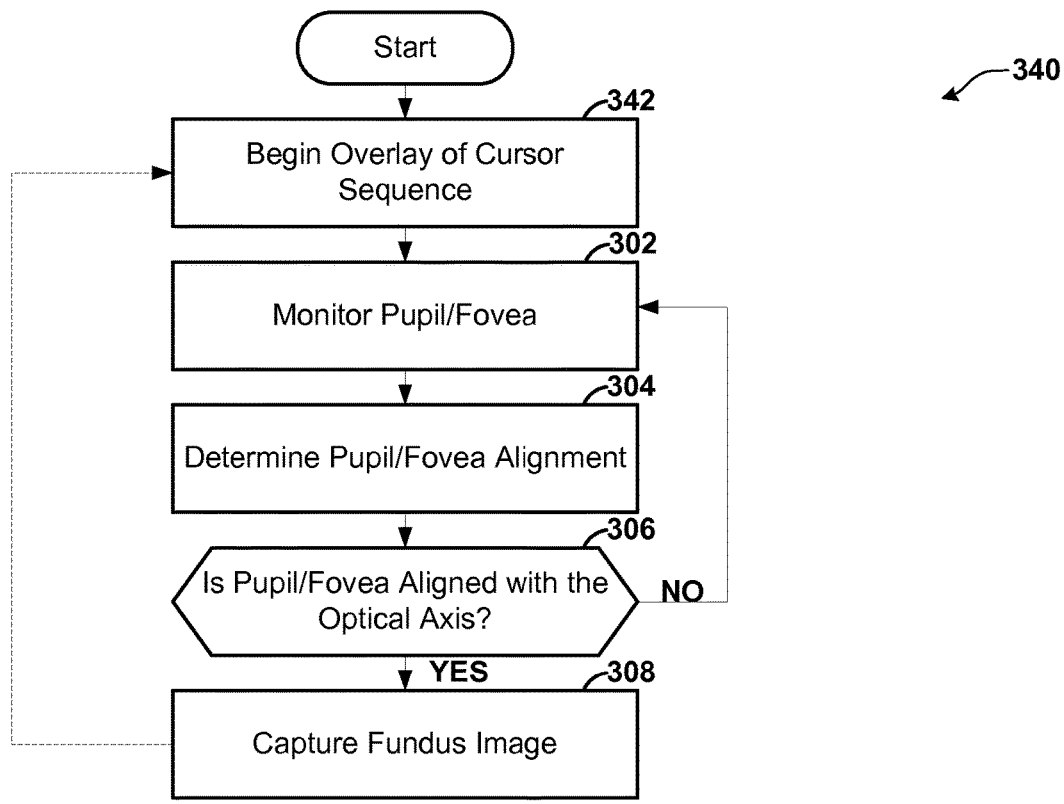
FIG. 12 shows another example process of capturing eye fundus images with the system of FIG. 1.

Referring now to FIG. 12, a process 340 performed using some embodiments of the ophthalmoscope device 102 is shown. The process 340 operates to image the fundus of the subject S using open-loop reverse eye tracking. The process 340 is similar to the process 300 illustrated and described with respect to FIG. 11, except that a cursor sequence is overlaid on the field of view of the subject S.

Initially, at step 342, the display device 134 begins to overlay a cursor sequence in the field of view of the subject. The cursor sequence includes a plurality of frames wherein an overlay image of a cursor is disposed at different locations. The display device 134 continues to display the cursor sequence throughout the process 340. During the process 340, the subject may be instructed to follow the cursor. The cursor sequence is designed to orient the pupil and fovea of the subject for fundus imaging. An example cursor sequence is shown and described in greater detail with respect to FIG. 13.

Next, in steps 302-308, a fundus image is captured as described with respect to FIG. 11.

Figure 13:
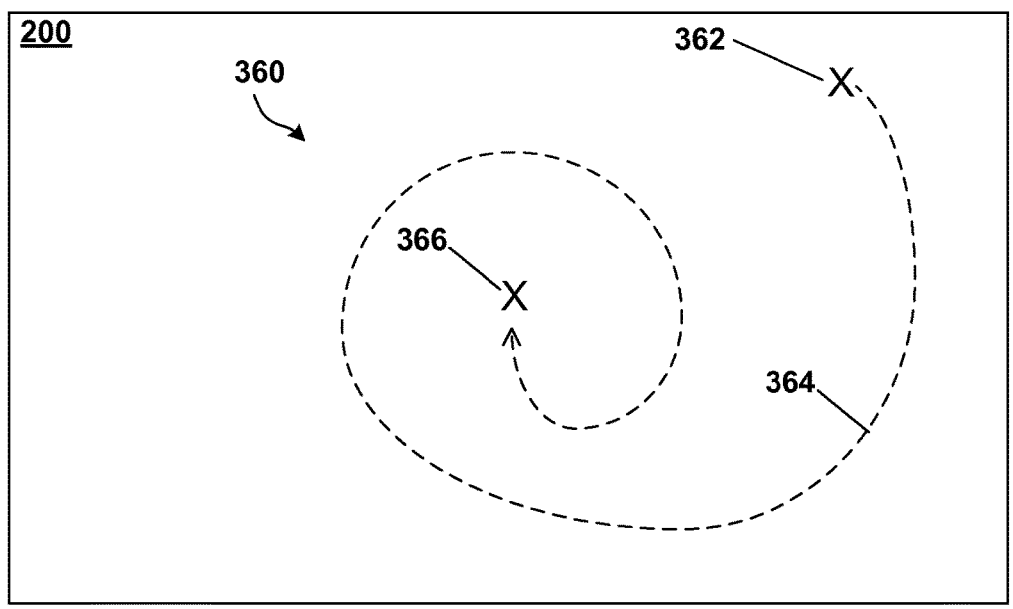
FIG. 13 shows an example cursor sequence from the process of FIG. 12.

Referring now to FIG. 13, an example cursor sequence 360 on the overlay layer 200 is illustrated. The cursor sequence 360 corresponds to a plurality frames that are displayed on the overlay layer. The frames illustrate the cursor at different locations on the overlay layer 200.

In the example cursor sequence 360, a cursor is initially shown at the starting position 362. In the frames that follow, the cursor moves along the path 364 until it reaches the ending position 366. The path 364 spirals into the ending position 366. In this manner, the pupil/fovea alignment of the subject S following the cursor will be drawn into many potential orientations for imaging.

The path 364 is just one example cursor sequence. In other embodiments, other cursor sequences are used.

Figure 14:
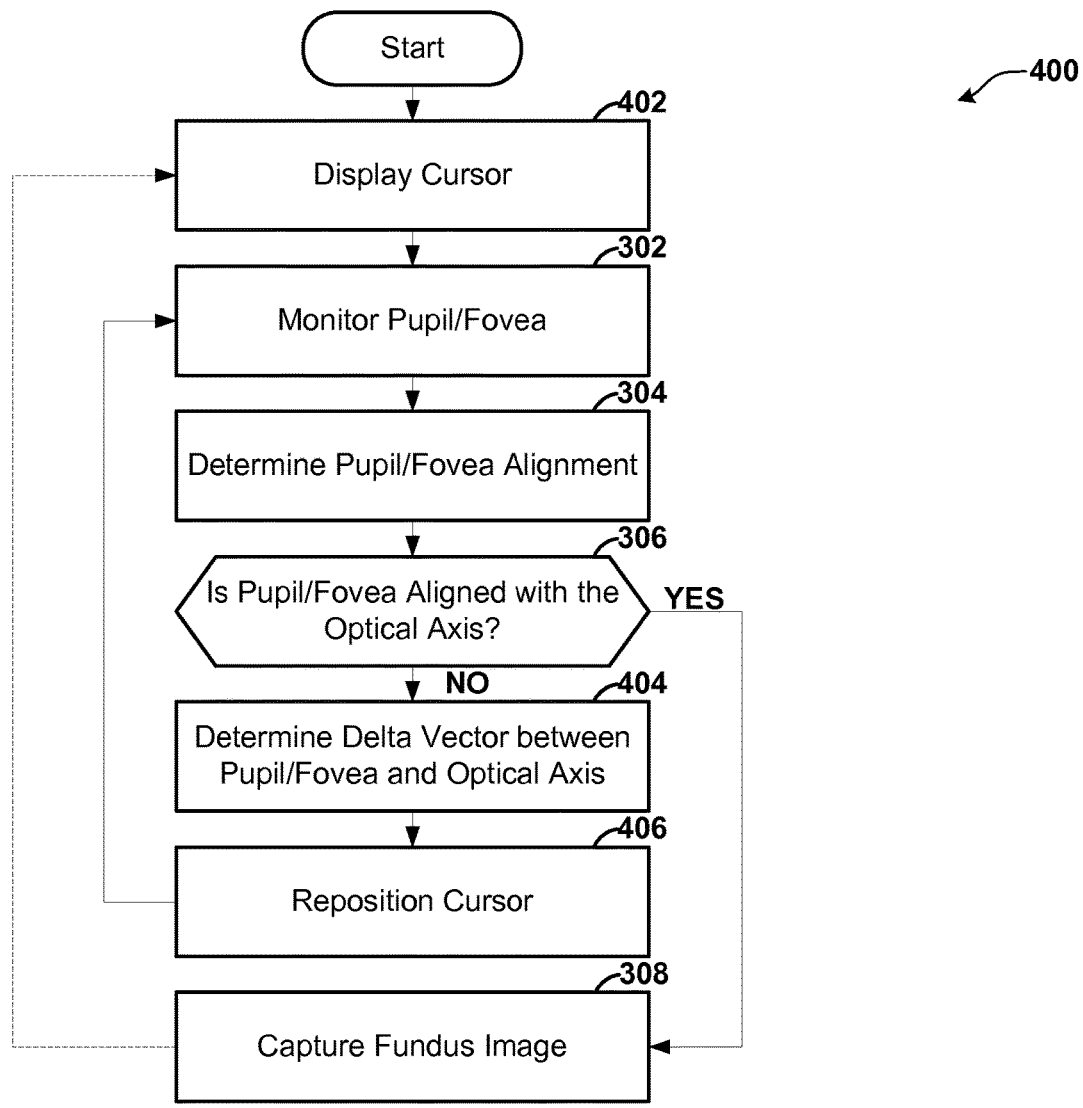
FIG. 14 shows another example process of capturing eye fundus images with the system of FIG. 1.

Referring now to FIG. 14, a process 400 performed using some embodiments of the ophthalmoscope device 102 is shown. The process 400 operates to image the fundus of the subject S using closed-loop reverse eye tracking. The process 400 is similar to the process 340 illustrated and described with respect to FIG. 12, except that the cursor sequence is dynamically generated based on determining the pupil/fovea alignment.

Initially, at step 402, the display device 134 overlays a cursor image in the field of view of the subject. During the process 400, the subject may be instructed to follow the cursor. The display device 134 continues to display the cursor at various locations throughout the process 400.

Next, in steps 302-306, the pupil/fovea orientation is determined and compared to the optical axis of the image capture device 136 as described with respect to FIG. 11. If the pupil/fovea orientation is substantially aligned with the optical axis of the image capture device 136, the process proceeds to step 308 to capture a fundus image as described with respect to FIG. 11. If not, the process continues to steps 404-406 to reposition the cursor.

At step 404, a delta vector between the pupil/fovea orientation axis 292 and the optical axis 290 is determined. The delta vector corresponds to the difference in position between the current location of the pupil and a desired location of the pupil for fundus imaging. In some embodiments, the desired location is an estimated optimal location for imaging of the fundus.

Next, at step 406, the cursor is repositioned by a vector that corresponds to the delta vector. In some embodiments, the vector by which the cursor is repositioned on the overlay layer 200 is calculated by scaling the delta vector by a factor that correlates a distance on the overlay layer 200 to a pupil movement distance. After the cursor is repositioned, steps 302-306 are repeated to determine whether the pupil/fovea is now aligned for imaging the fundus. If not, steps 404-406 are repeated again as well. These steps are repeated until the fundus image can be captured. An example sequence of cursor positions is shown and described in greater detail with respect to FIG. 15.

Figure 15:
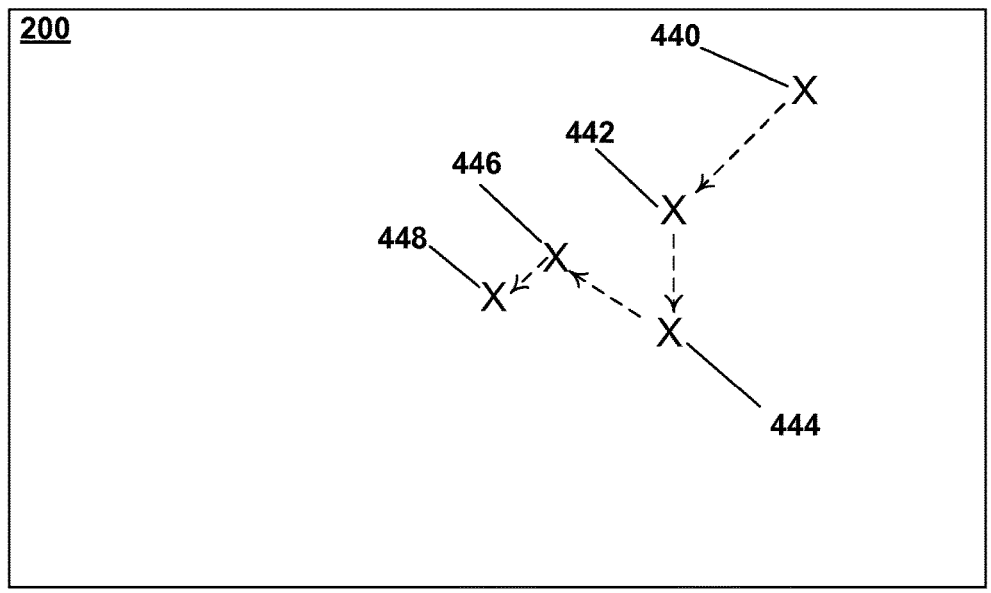
FIG. 15 shows an example sequence of cursor positions from the process of FIG. 14.

Referring now to FIG. 15, an example sequence of cursor positions on the overlay layer 200 is illustrated. Each of the cursor positions shown corresponds to a cursor location during various example iterations of process 400.

In the example, the cursor starts at position 440. After determining in step 306 that the pupil/fovea orientation is not aligned for fundus imaging, the cursor is repositioned to location 442. These steps repeat as the cursor moves to positions 444, 446, and finally 448. When the cursor is display at position 448, step 306 determines that the pupil/fovea orientation is aligned properly for fundus imaging. Accordingly, the fundus image is captured.

The cursor positions shown in FIG. 15 are merely examples. In various embodiments, the cursor may be displayed in other positions as well.

Figure 16:
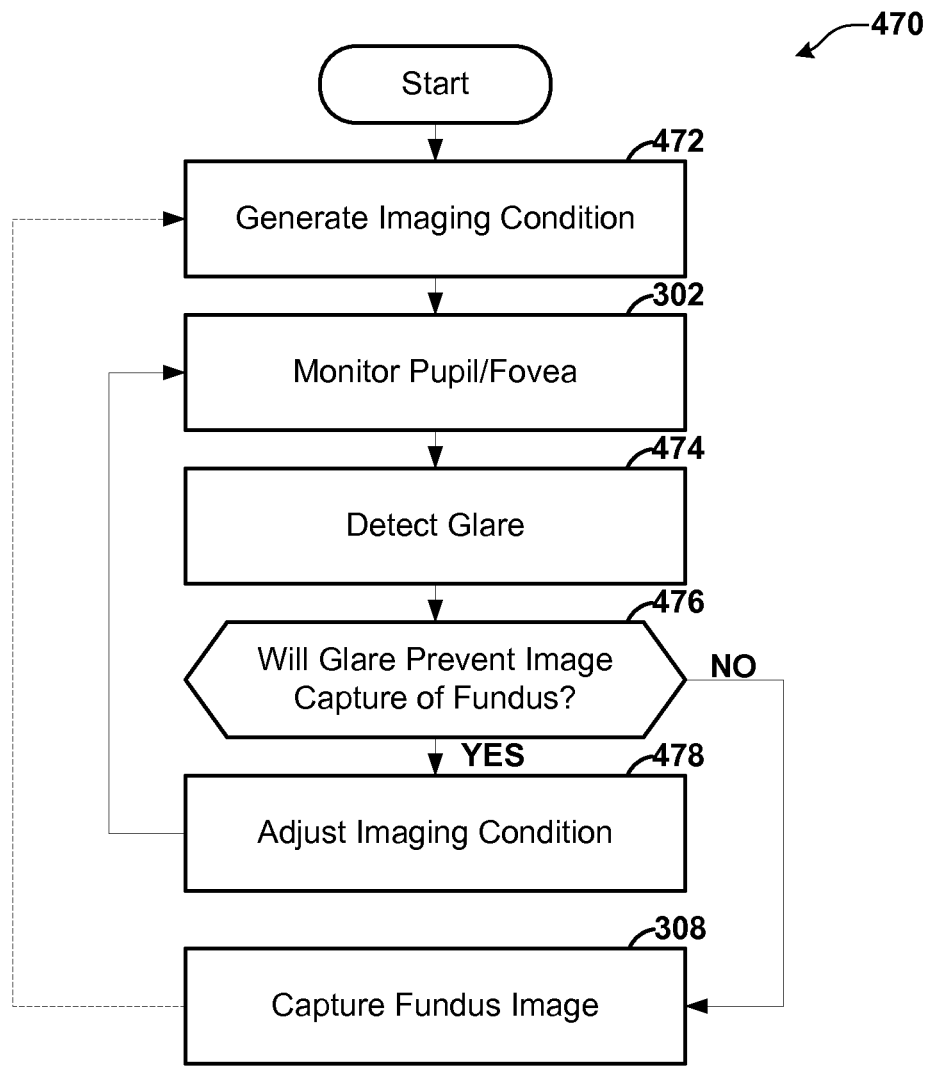
FIG. 16 shows another example process of capturing eye fundus images with the system of FIG. 1.

Referring now to FIG. 16, a process 470 performed using some embodiments of the ophthalmoscope device 102 is shown. The process 470 operates to image the fundus of the subject S while eliminating glare. Glare (i.e., light reflected off of the surface of the eye of the subject) may interfere with imaging the fundus.

Initially, at step 472, the device 102 generates an imaging condition. In some embodiments, the imaging condition is generated by the display device 134 displaying an illumination pattern. The illumination pattern is a pattern of light designed to illuminate the eye or a portion of the eye of the subject S. In some embodiments, the illumination pattern includes bright dots or bright regions on the overlay layer. Other embodiments of the illumination pattern are possible as well. In other embodiments, the illumination pattern is generated by the illumination device 138 instead of or in addition to the display device 134.

Next, at step 302, the pupil or fovea or both of the subject S are monitored as described with respect to FIG. 11.

Next, at step 474, the control module 132 processes at least a portion of the images captured by the image capture device 136. The control module 132 processes the images to identify regions of glare in the image. Glare regions may be detected using various image processing techniques. For example, in some embodiments, glare regions are detected as regions of the image with a saturation level above a defined threshold. Other embodiments of the glare detection step are possible as well.

Next, at step 476, the regions of glare are evaluated to determine whether they will interfere with imaging of the fundus. In some embodiments, this step is performed by determining whether the fovea is visible despite the regions of glare in the image. If the detected regions of glare interfere with fundus imaging, step 478 is performed to adjust the illumination pattern. If not, step 308 is performed as described with respect to FIG. 11 to capture a fundus image.

At step 478, the imaging condition is adjusted. In some embodiments, the imaging condition is adjusted by adjusting the illumination pattern. In some embodiments, the illumination pattern is adjusted according to a pre-defined sequence. For example, some embodiments include a sequence of pre-defined illumination patterns that may be displayed during process 470 as necessary. In other embodiments, the illumination pattern is adjusted based on determining a delta vector for a glare region. For example, the delta vector may correspond to the difference between the current glare region and a location where the glare would not interfere with imaging the fundus. After the illumination pattern is adjusted, steps 302, 474, and 476 are repeated to determine if the fundus image can be captured with the adjusted illumination pattern.

In other embodiments, glare is removed by adjusting the view angle or depth of field of the image capture device 136. For example, in some embodiments, the depth of field is adjusted by moving the lens 164 along the optical axis 290 towards or away from the subject S, such as with auto-focusing mechanisms. Additionally, in some embodiments, the view angle of the image capture device 136 is adjusted using optical stabilizer technologies, such as double prism actuators or direction actuated fluid lenses. In these embodiments, the imaging condition of step 472 comprises first configurations of the view angle and depth of field. If detected glare prevents imaging of the fundus, the imaging condition is adjusted by adjusting the depth of field, the view angle, or both in step 478. Then another image is captured. This process repeats until an image is captured where glare does not prevent imaging of the fundus. In some embodiments, the configurations of the depth of field and view angle are adjusted according to a pre-defined sequence. In other embodiments, the configurations of the depth of field and view angle are adjusted based on determining a delta vector for a glare region.

Figure 17:
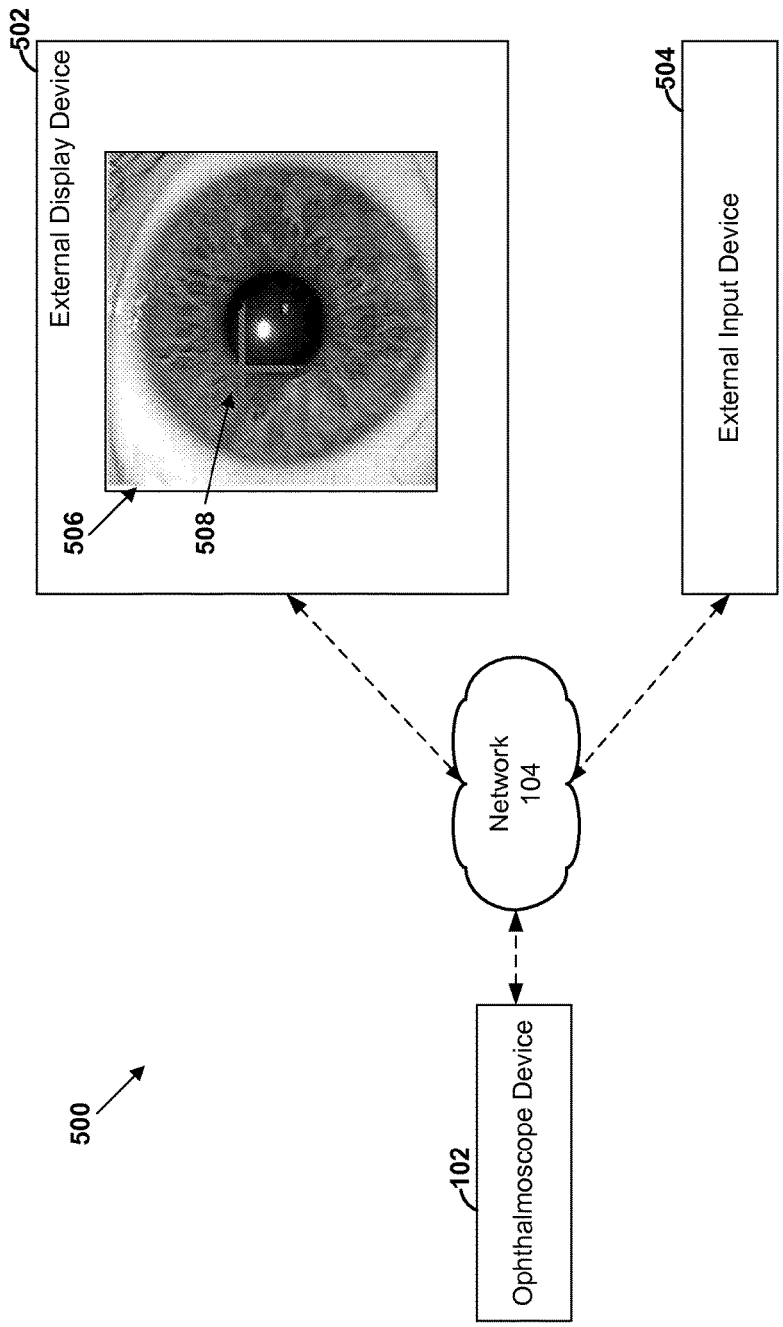
FIG. 17 shows another example system for performing ophthalmoscopy procedures.

FIG. 17 is another example system 500 for performing ophthalmoscopy procedures. The example system 500 includes the ophthalmoscope device 102, an external display device 502, and an external input device 504.

The ophthalmoscope device 102 is a wearable device to capture images of the eye fundus and is illustrated and described in greater detail with respect to FIGS. 2-8. In system 500, the ophthalmoscope device 102 is configured to transmit images it captures to the external display device 502 and to receive input commands from the external input device 504.

In some embodiments, the ophthalmoscope device 102 also transmits a location corresponding to the location of the cursor on the overlay layer 200 to the external display device 502. In some embodiments, the cursor location is transmitted as part of the image. For example, in some embodiments, the cursor is overlaid on the transmitted images. In other embodiments, the cursor location is transmitted as coordinate information.

In various embodiments, the external display device 502 is implemented as various types of display devices. Example types of display devices include, but are not limited to, cathode-ray tube displays, LCD display panels, plasma screen display panels, touch-sensitive display panels, LED screens, projectors, and other types of display devices. The external display device 502 is configured to receive and display images transmitted by the ophthalmoscope device 102. In this manner, the external display device 502 permits a caregiver or another person to view the images captured by the ophthalmoscope device 102. The example external display device 502 is displaying an image 506 of an eye and a cursor 508.

The external input device 504 is a component that provides user input to the ophthalmoscope device 102. Example types of input devices include, but are not limited to, keyboards, mice, trackballs, stylus input devices, key pads, microphones, joysticks, touch-sensitive display screens, and other types of devices that provide user input. In some embodiments, the external input device 504 is integral with the external display device 502, while in other embodiments the external display device 502 and the external input device 504 are separate devices.

In some embodiments, the external input device 504 provides reposition commands to the ophthalmoscope device 102. The reposition commands direct the ophthalmoscope device 102 to reposition the cursor 202 on the overlay layer 200. In some embodiments, the reposition command includes new coordinates for the cursor 202. In other embodiments, the reposition command includes a delta vector for the cursor 202. Yet other embodiments are possible as well. Using the reposition commands, a caregiver can direct the eye of the subject S to a desired location for imaging.

In some embodiments, the external input device 504 provides image capture commands to the ophthalmoscope device 102. The image capture command directs the ophthalmoscope device 102 to capture a fundus image. Using the image capture command, a caregiver can capture a fundus image at any desired orientation.

In some embodiments, the ophthalmoscope device 102 communicates directly with the external display device 502 and the external input device 504. For example, in some embodiments, the ophthalmoscope device 102 communicates directly with the external display device 502 and the external input device 504 using Bluetooth. Other embodiments are possible as well.

Figure 18:
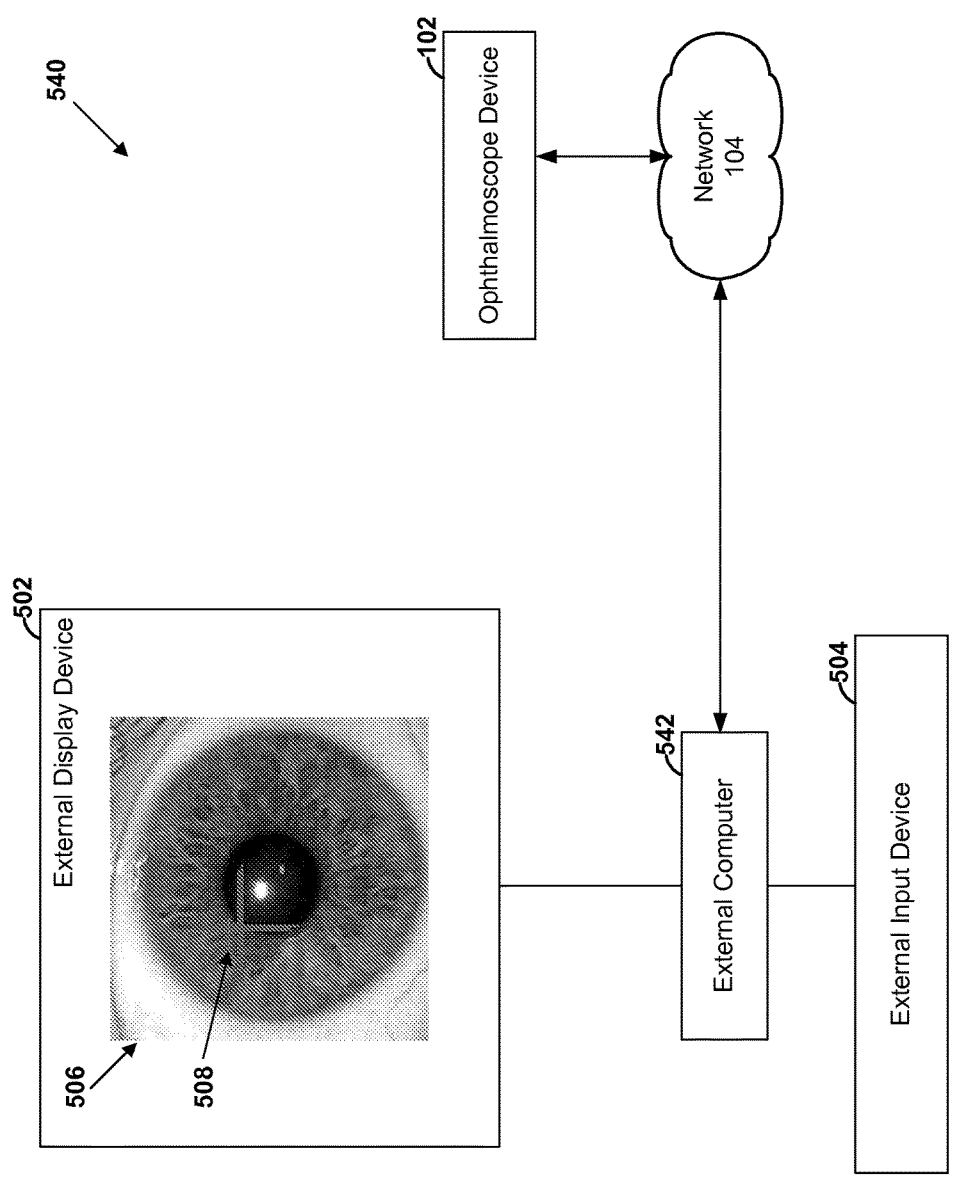
FIG. 18 shows an example system for performing ophthalmoscopy procedures.

FIG. 18 is another example system 540 for performing ophthalmoscopy procedures. The example system 540 includes the ophthalmoscope device 102, the external display device 502, the external input device 504, and an external computer 542. The system 540 is similar to the system 500, except that the ophthalmoscope device 102 communicates with the external computer 542 rather than the external display device 502, and the external input device 504.

The external computer 542 is a computing device. Computing devices are described in detail with respect to FIG. 1. In some embodiments, the external computer 542 runs a software application to communicate with the ophthalmoscope device 102. The computing device is configured to cause the external display device 502 to display images that have been transmitted to the external computer 542 by the ophthalmoscope device 102. Similarly, the external computer 542 is configured to receive input from the external input device 504 and transmits that input to the ophthalmoscope device 102.

In some embodiments, the external display device 502 and external input device 504 are integral with the external computer 542. For example, in some embodiments, the external computer 542 is an iPhone or iPad, both from Apple Inc. of Cupertino, Calif. Yet in other embodiments, the external computer 542 is a different portable computing device, such as a tablet computer running an operating system like the Microsoft Windows operating system from Microsoft Corporation of Redmond, Wash., or the Android operating system from Google Inc. of Mountain View, Calif. Yet other embodiments of the external computer 542 are possible as well.

Figure 19:
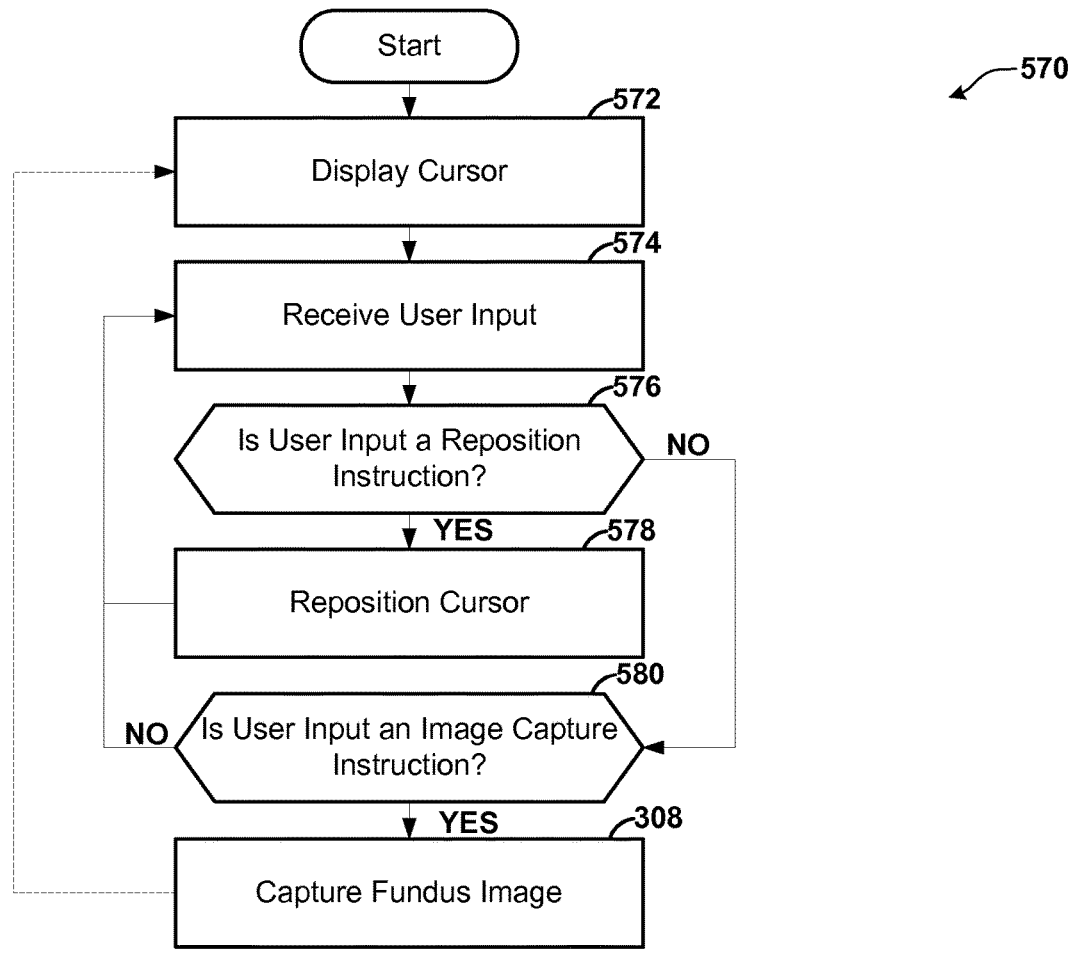
FIG. 19 shows a method of capturing eye fundus images with the systems of FIG. 17 and FIG. 18.

Referring now to FIG. 19, a process 570 performed using some embodiments of the system 500 or system 540 is shown. The process 570 operates to image the fundus of the subject S using a user directed path.

Initially, at step 572, an image of the cursor 202 is displayed on the overlay layer 200. This step is similar to step 402 and is described in more detail with respect to FIG. 14. The image of the cursor 202 is displayed throughout the process 570.

Next, at step 574, user input is received. In some embodiments, the user input is received directly from an external input device 504. In other embodiments, the user input is received from an external computer 542.

Next, at step 576, it is determined whether the user input is a reposition command. If the user input is a reposition command, then step 578 is performed to reposition the cursor. If not, then step 580 is performed to determine whether the user input is an image capture command.

At step 578, the image of the cursor 202 is repositioned on the overlay layer. In this manner, a caregiver can direct the orientation of the eye of the subject. After step 578, step 574 is performed to receive more user input.

At step 580, it is determined whether the user input is an image capture command. If the user input is an image capture command, the step 308 is performed to capture a fundus image as described with respect to FIG. 11. If not, the step 574 is performed to receive more user input.

In other embodiments of the process 570, step 580 is not performed. Instead, the image is captured using passive eye tracking. For example, in some embodiments the process 300 is used in combination with the steps 572-578. The process 300 is shown and described in greater detail with respect to FIG. 11.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. An eye fundus imaging apparatus, comprising:
    a display device;
    an image capture device configured to capture at least one image of a fundus of an eye; and
    a control module that:
        displays a target, the target indicating a desired position for the image capture device to capture the at least one image of the fundus of the eye;
        monitors a relative position of the eye with respect to the target; and
        when the relative position of the eye corresponds to the target, automatically captures the at least one image of the fundus of the eye.

2. The eye fundus imaging apparatus of claim 1, wherein the eye fundus imaging apparatus is a handheld apparatus.

3. The eye fundus imaging apparatus of claim 1, wherein the control module further automatically captures the at least one image of the fundus of the eye when the eye is aligned with the target.

4. The eye fundus imaging apparatus of claim 3, wherein the control module further automatically captures the at least one image of the fundus of the eye when a pupil of the eye is aligned with the target.

5. The eye fundus imaging apparatus of claim 1, wherein the control module further displays the target for a pupil of the eye.

6. The eye fundus imaging apparatus of claim 1, wherein the target is a cursor.

7. The eye fundus imaging apparatus of claim 1, wherein the eye fundus imaging apparatus is a wearable apparatus.

* * * * *

UNITED STATES PATENT AND TRADEMARK OFFICE
CERTIFICATE OF CORRECTION

PATENT NO. : 10,335,029 B2
APPLICATION NO. : 15/971693
DATED : July 2, 2019
INVENTOR(S) : Wang et al.

It is certified that error appears in the above-identified patent and that said Letters Patent is hereby corrected as shown below:

On the Title Page

Line 1, Title: Delete "Opthalmoscope" and insert --Ophthalmoscope--

Page 3, Line 38, References Cited, Other Publications: Delete "scnaning" and insert --scanning--

Page 3, Line 41, References Cited, Other Publications: Delete "Stablized" and insert --Stabilized--

Page 4, Line 7, References Cited, Other Publications: Delete "Visison" and insert --Vision--

In the Specification

Column 1, Line 1: Delete "Opthalmoscope" and insert --Ophthalmoscope--

Signed and Sealed this
Seventeenth Day of September, 2019

Andrei Iancu
*Director of the United States Patent and Trademark Office*